(12) United States Patent
Uber, III

(10) Patent No.: US 9,436,989 B2
(45) Date of Patent: Sep. 6, 2016

(54) SYSTEM AND METHOD FOR RAPID QUANTITATIVE DYNAMIC MOLECULAR IMAGING SCANS

(75) Inventor: Arthur E. Uber, III, Pittsburgh, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 230 days.

(21) Appl. No.: 14/123,390

(22) PCT Filed: Jun. 4, 2012

(86) PCT No.: PCT/US2012/040755
§ 371 (c)(1),
(2), (4) Date: Dec. 12, 2013

(87) PCT Pub. No.: WO2012/167257
PCT Pub. Date: Dec. 6, 2012

(65) Prior Publication Data
US 2014/0119621 A1    May 1, 2014

Related U.S. Application Data

(60) Provisional application No. 61/493,142, filed on Jun. 3, 2011, provisional application No. 61/629,414, filed on Nov. 18, 2011.

(51) Int. Cl.
*G06K 9/00* (2006.01)
*G06T 7/00* (2006.01)
(Continued)

(52) U.S. Cl.
CPC ............ *G06T 7/0012* (2013.01); *A61B 6/032* (2013.01); *A61B 6/037* (2013.01); *A61B 6/481* (2013.01);
(Continued)

(58) Field of Classification Search
USPC .................................................. 382/128–134
See application file for complete search history.

(56) References Cited

U.S. PATENT DOCUMENTS 3,191,789 A   6/1965   Davidson
4,092,546 A   5/1978   Larrabee
(Continued)

FOREIGN PATENT DOCUMENTS

FR         2867084 A1     9/2005
WO      2006129301 A2    12/2006
WO      2009042577 A2     4/2009

OTHER PUBLICATIONS

International Search Report with Written Opinion for International Application No. PCT/US2012/040755 mailed on Aug. 10, 2012.
(Continued)

*Primary Examiner* — Alex Liew
(74) *Attorney, Agent, or Firm* — Joseph L. Kent; David Schramm; James R. Stevenson

(57) ABSTRACT

Methods and systems for controlled administration of a tracer and quantification of uptake of the tracer by a target organ are described. The method includes administering a tracer to a patient and imaging at least two regions of the patient's body that cannot be imaged simultaneously. An input function for the tracer can be determined by imaging a first region of the patient's body during selected times, and using an injector to administer the tracer in a manner that accurately estimates the input function when this first region is not being imaged. One or more additional regions of the body may then be imaged to create data that may be used to estimate the input function. One or more parameters may then be estimated from each additional region of the body based on the input function and the imaging data gathered from each region.

16 Claims, 9 Drawing Sheets

(51) Int. Cl.

| | | |
|---|---|---|
| *A61K 49/00* | (2006.01) | |
| *A61B 6/03* | (2006.01) | |
| *A61B 6/00* | (2006.01) | |
| *A61B 5/00* | (2006.01) | |
| *A61B 5/0402* | (2006.01) | |
| *A61B 5/055* | (2006.01) | |
| *G01R 33/56* | (2006.01) | |
| *G06F 19/00* | (2011.01) | |

(52) U.S. Cl.
CPC ............. *A61B 6/486* (2013.01); *A61B 6/503* (2013.01); *A61B 6/507* (2013.01); *A61B 6/5217* (2013.01); *A61K 49/0002* (2013.01); *A61B 5/0402* (2013.01); *A61B 5/055* (2013.01); *A61B 5/0555* (2013.01); *A61B 5/7285* (2013.01); *A61B 6/5288* (2013.01); *A61B 2576/023* (2013.01); *G01R 33/5601* (2013.01); *G06F 19/3468* (2013.01)

(56) References Cited

U.S. PATENT DOCUMENTS

| | | | |
|---|---|---|---|
| 4,405,163 A | 9/1983 | Voges et al. | |
| 4,405,312 A | 9/1983 | Gross et al. | |
| 4,409,488 A | 10/1983 | King | |
| 4,467,588 A | 8/1984 | Carveth | |
| 4,512,764 A | 4/1985 | Wunsch | |
| 4,529,401 A | 7/1985 | Leslie et al. | |
| 4,563,175 A | 1/1986 | LaFond | |
| 4,585,941 A | 4/1986 | Bergner | |
| 4,632,123 A | 12/1986 | Govaert et al. | |
| 4,645,073 A | 2/1987 | Homan | |
| 4,747,826 A | 5/1988 | Sassano | |
| 4,853,546 A | 8/1989 | Abe et al. | |
| 4,925,444 A | 5/1990 | Orkin et al. | |
| 4,936,841 A | 6/1990 | Aoki et al. | |
| 4,966,579 A | 10/1990 | Polaschegg | |
| 5,145,083 A | 9/1992 | Takahashi | |
| 5,190,522 A | 3/1993 | Wojcicki et al. | |
| 5,242,403 A | 9/1993 | Falb et al. | |
| 5,274,239 A | 12/1993 | Lane et al. | |
| 5,342,346 A | 8/1994 | Honda et al. | |
| 5,472,403 A | 12/1995 | Cornacchia et al. | |
| 5,492,147 A | 2/1996 | Challender et al. | |
| 5,583,902 A | 12/1996 | Bae | |
| 5,687,208 A | 11/1997 | Bae et al. | |
| 5,806,519 A | 9/1998 | Evans, III et al. | |
| 5,840,026 A | 11/1998 | Uber, III et al. | |
| 5,938,636 A | 8/1999 | Kramer et al. | |
| 6,055,985 A | 5/2000 | Bae et al. | |
| 6,162,198 A | 12/2000 | Coffey et al. | |
| 6,238,374 B1 | 5/2001 | Winkler | |
| 6,353,803 B1* | 3/2002 | Degani .................. G06T 7/0012 | |
| | | | 702/100 |
| 6,362,472 B1 | 3/2002 | Yarnall et al. | |
| 6,385,483 B1 | 5/2002 | Uber, III et al. | |
| 6,471,674 B1 | 10/2002 | Emig et al. | |
| 6,547,787 B1 | 4/2003 | Altman et al. | |
| 6,602,488 B1 | 8/2003 | Daghighian | |
| 6,689,091 B2 | 2/2004 | Bui et al. | |
| 6,699,219 B2 | 3/2004 | Emig et al. | |
| 6,767,319 B2 | 7/2004 | Reilly et al. | |
| 6,889,074 B2 | 5/2005 | Uber, III et al. | |
| 6,972,001 B2 | 12/2005 | Emig et al. | |
| 7,169,135 B2 | 1/2007 | Duchon et al. | |
| 7,204,797 B2 | 4/2007 | Reilly et al. | |
| 7,268,359 B2 | 9/2007 | Fu et al. | |
| 7,313,431 B2 | 12/2007 | Uber, III et al. | |
| 7,335,902 B2 | 2/2008 | Soundararajan | |
| 7,457,804 B2 | 11/2008 | Uber, III et al. | |
| 7,712,491 B2 | 5/2010 | Tochon-Danguy et al. | |
| 8,198,599 B2 | 6/2012 | Bouton et al. | |
| 8,454,561 B2 | 6/2013 | Uber, III et al. | |

| | | | |
|---|---|---|---|
| 2002/0029120 A1* | 3/2002 | Degani ................ A61B 5/0263 | |
| | | | 702/100 |
| 2002/0168317 A1 | 11/2002 | Daighighian et al. | |
| 2003/0105605 A1* | 6/2003 | Degani .................. G06T 7/0012 | |
| | | | 702/104 |
| 2004/0054248 A1 | 3/2004 | Kimchy et al. | |
| 2004/0082918 A1 | 4/2004 | Evans et al. | |
| 2004/0176676 A1 | 9/2004 | Graw | |
| 2004/0205343 A1 | 10/2004 | Forth et al. | |
| 2004/0254525 A1 | 12/2004 | Uber, III et al. | |
| 2004/0260143 A1 | 12/2004 | Reilly et al. | |
| 2005/0085682 A1 | 4/2005 | Sasaki et al. | |
| 2005/0129170 A1 | 6/2005 | Watson et al. | |
| 2005/0203329 A1 | 9/2005 | Muto et al. | |
| 2005/0238576 A1 | 10/2005 | Dell et al. | |
| 2006/0004243 A1 | 1/2006 | Shimizu et al. | |
| 2007/0255135 A1* | 11/2007 | Kalafut .............. A61B 5/02028 | |
| | | | 600/431 |
| 2008/0013814 A1* | 1/2008 | Carlsen ................. G06T 7/0034 | |
| | | | 382/131 |
| 2008/0038839 A1 | 2/2008 | Linder et al. | |
| 2008/0042067 A1 | 2/2008 | Rousso et al. | |
| 2008/0125643 A1 | 5/2008 | Huisman et al. | |
| 2008/0131362 A1 | 6/2008 | Rousso et al. | |
| 2008/0200747 A1 | 8/2008 | Wagner et al. | |
| 2008/0242915 A1 | 10/2008 | Jackson et al. | |
| 2009/0116711 A1* | 5/2009 | Larson .................. G06T 7/0016 | |
| | | | 382/128 |
| 2009/0257949 A1 | 10/2009 | Hefti et al. | |
| 2010/0021378 A1 | 1/2010 | Rousso et al. | |
| 2010/0054559 A1* | 3/2010 | Narayanan ............ G06T 7/2033 | |
| | | | 382/128 |
| 2010/0185040 A1 | 7/2010 | Uber, III et al. | |
| 2010/0232662 A1* | 9/2010 | Spies .................. A61B 5/02755 | |
| | | | 382/131 |
| 2011/0066024 A1* | 3/2011 | Shih ..................... G06F 19/321 | |
| | | | 600/410 |
| 2011/0076317 A1 | 3/2011 | Alessi et al. | |
| 2011/0178359 A1 | 7/2011 | Hirschman et al. | |
| 2013/0079581 A1 | 3/2013 | Agamaite et al. | |
| 2013/0123567 A1 | 5/2013 | Agamaite et al. | |
| 2013/0124103 A1 | 5/2013 | Mabie et al. | |
| 2014/0241604 A1* | 8/2014 | Wang ................... A61B 5/0263 | |
| | | | 382/131 |

OTHER PUBLICATIONS

Beaulieu, S., et al., "SUV Varies with Time After Injection in 18F-FDG PET of Breast Cancer: Characterization and Method to Adjust for Time Differences," Journal of Nuclear Medicine, vol. 44, No. 7, pp. 1044-1050 (Jul. 2003).

Strauss, L.G., et al., "Shortened PET Data Acquisition Protocol for the Quantification of 18F-FDG Kinetics," Journal of Nuclear Medicine, vol. 44, No. 12, pp. 1933-1939 (2003).

Iida, H., et al., "Absolute quantitation of myocardial blood flow with (201)Tl and dynamic SPECT in canine: optimisation and validation of kinetic modeling," Journal of Nuclear Medicine & Molecular Imaging, vol. 35, pp. 896-905 (2008).

Cochet, A., et al., "Evaluation of Breast Tumor Blood Flow with Dynamic First-Pass 18F-FDG PET/CT: Comparison with Angiogenesis Markers and Prognostic Factors," Journal of Nuclear Medicine, vol. 53, Feb. 17, 2012.

Mullani, N. et al., "Tumor Blood Flow Measured by PET Dynamic Imaging of First-Pass 18F-FDG Uptake: A Comparison with 15O-Labeled Water-Measured Blood Flow," Journal of Nuclear Medicine, vol. 49, No. 4, Apr. 2008.

Khorsand, A., et al., "Assessment of myocardial perfusion by dynamic N-13 ammonia PET imaging: Comparison of 2 tracer kinetic models," American Society of Nuclear Cardiology, pp. 410-417, 2005.

Mullani, N., et al., "First-Pass Measurements of Regional Blood Flow with External Detectors," Journal of Nuclear Medicine, vol. 24, No. 7, pp. 557-581, 1983.

Vriens, D., et al., "Methodological considerations in quantification of oncological FDG PET studies," Eur J Nucl Med Mol Imaging, vol. 37, pp. 1408-1425, 2010.

(56) References Cited

OTHER PUBLICATIONS

Klein, R., et al., "Quantification of myocardial blood flow and flow reserve: Technical aspects," Journal of Nuclear Cardiology, vol. 17, pp. 555-570, Jul./Aug. 2010.
Dekemp, R., et al., "Constant-Activity-Rate Infusions for Myocardial Blood Flow Quantification with 82Rb and 3D PET," 2006 IEEE Nuclear Science Symposium Conference Record, pp. 3519-3521.
Schuleri, K., et al., "Assessment of coronary blood flow with computed tomography and magnetic resonance imaging," Journal of Nuclear Cardiology, vol. 17, pp. 582-590, 2010.
Liukko, K., et al., "Correction for time delay between PET and blood data," Turku PET Centre Modelling Report, 2007.
Measurement of liver blood flow using [15O]H2O and PET, Power Point Presentation, Literature review, Turku PET Center, 2005.
Choi, Y., et al., "Evaluation of the Effect of Glucose Ingestion and Kinetic Model Configurations of FDG in the Normal Liver," Journal of Nuclear Medicine, vol. 35, pp. 818-823., 1994.
Bae, K., et al., "Multiphasic Injection Method for Uniform Prolonged Vascular Enhancement at CT Angiography: Pharmacokinetic Analysis and Experimental Porcine Model," Radiology, vol. 216, No. 3, pp. 872-880, Sep. 2000.
Bae, K., "Peak Contrast Enhancement in CT and MR Angiography: When does it Occur and Why? Pharmacokinetic Study in a Procine Model," Radiology, vol. 227, pp. 809-816, Jun. 2003.
Dougherty, D., et al., "Ventromedial Prefrontal Cortex and Amygdala Dysfunction During an Anger Induction Positron Emission Tomography Study in Patients With Major Depressive Disorder With Anger Attacks," Arch Gen Psychiatry, vol. 61, pp. 795-804, 2004.
Vesselle, H., et al., "F-Fluorothymidine Radiation Dosimetry in Human PET Imaging Studies," Journal of Nuclear Medicine, vol. 44, No. 9, pp. 1482-1488, Sep. 2003.
Schwilden, H., "A General Method for Calculating the Dosage Scheme in Linear Pharmacokinetics," European Journal of Clinical Pharmacology, vol. 20, pp. 379-386, 1981.
Graham, M., et al., "Comparison of Simplified Quantitative Analyses of FDG Uptake," Nuclear Medicine & Biology, vol. 27, pp. 647-655, 2000.
Mankoff, D., et al., "A Graphical Analysis Method to Estimate Blood-to-Tissue Transfer Constants for Tracers with Labeled Metabolites," Journal of Nuclear Medicine, vol. 37, pp. 2049-2057, 1996.
Logan, J., et al., "Graphical Analysis of reversible Radioligand Binding from Time-Activity Measurements Applied to [N-11C-methyl]-(-)-Cocaine PET Studies in Human Subjects," Journal of Cerebral Blood Flow and Metabolism, vol. 10, pp. 740-747, 1990.
"Multiple Time Graphical Analysis", available at http://www.turkupetcentre.fi, last visited May 28, 2012.
Hunter, G., et al., "Simplified Measurement of Deoxyglucose Utilization Rate", Journal of Nuclear Medicine, vol. 37, pp. 950-955, 1996.
Strauss, L., et. al., "Parametric imaging: a promising approach for evaluation of dynamic PET-18F-FDG studies—the DKFZ experience", Hellenic Journal of Nuclear Medicine, pp. 18-22, Jan.-Apr. 2010.
Strauss, L., et al., "The Applications of PET in Clinical Oncology", Journal of Nuclear Medicine, vol. 32, pp. 623-648, 1991.
Patlak, C., et al., "Graphical Evaluation of Blood-to-Brain Transfer Constants from Multiple-Time Uptake Data. Generalizations", Journal of Cerebral Blood Flow and Metabolism, vol. 5, pp. 584-590, 1985.
Disselhorst, J., et al., "Shortened Dynamic 18F-FDG PET", Journal of Nuclear Medicine, vol. 52, No. 8, Aug. 2011.
Visser, E., et al., "Shortened Dynamic FDG-PET Protocol to Determine the Glucose Metabolic Rate in Non=small Cell Lung Carcinoma", 2008 IEEE Nuclear Science Symposium Conference, pp. 4455-4458, 2008.
Uber, III, "Injectors Enabling New Imaging Procedures in Molecular Imaging", Power Point Presentation, Medrad Corporate Innovations, Jul. 1, 2011.
Eriksson, Olof, et al., A computerized Infusion Pump for control of tissue tracer concentration during Positron Emission Tomography in vivo Pharmacokinetic/Pharmacodynamic measurements. BMC Medical Physics, May 30, 2008 vol. 8., No. 1, p. 2.
Hiroyuki Ohba et al., Application of PET with feedback injection control system for quantification of drug-induced effects on the brain function, International Congress Series, Mar. 1, 2004, vol. 1264, p. 202-205.
Supplementary European Search Report from corresponding EP Application No. EP12792501.

\* cited by examiner

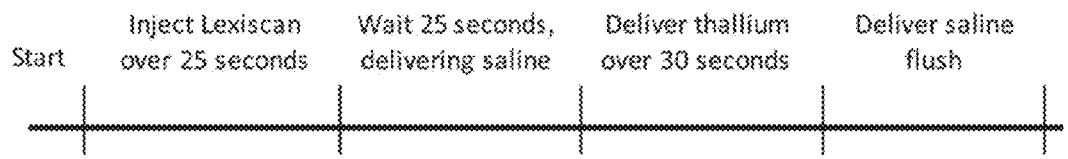
FIG. 4a
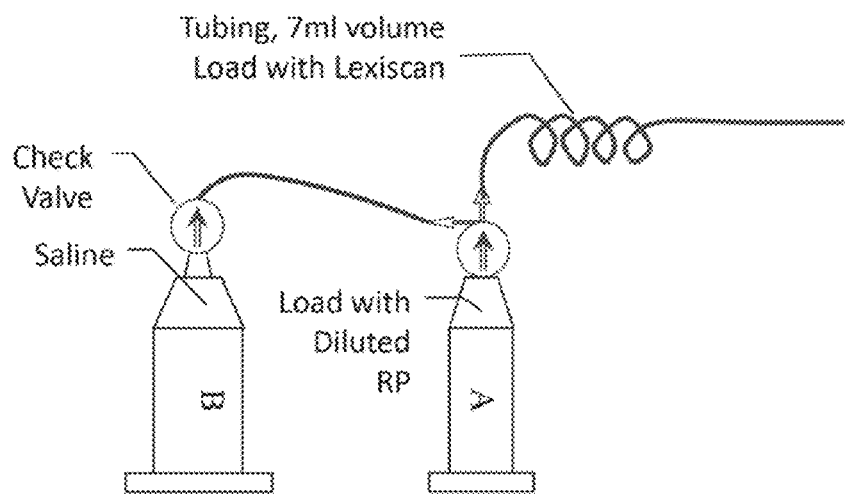
FIG. 4b
| Purpose | Phase | Volume | Flow Rate | Duration |
|---|---|---|---|---|
| Deliver Lexiscan | B | 5 ml | 0.2 ml/S | 25 S |
| Delay - Push residuals from vein & tubing. | B | 5 ml | 0.2 ml/S | 25 S |
| Delay - There will be about a 7 second delay before the thallium reaches the distal connector. Note: There should inherently be a small bubble at the start of the thallium. | | | | 7 S |
| Deliver Thallium | A | 30 ml | 1 ml/S | 30 S |
| Push residuals from vein & tubing. | B | 30 ml | 1 ml/S | 30 S |
FIG. 4c

SYSTEM AND METHOD FOR RAPID QUANTITATIVE DYNAMIC MOLECULAR IMAGING SCANS

CROSS-REFERENCE TO RELATED APPLICATIONS

This application is a 371 national phase application of PCT International Application No. PCT/US2012/40755, filed on Jun. 4, 2012, and designating the United States of America, which claims the benefit of U.S. Provisional Application Ser. No. 61/493,142, filed on Jun. 3, 2011, and U.S. Provisional Application Ser. No. 61/629,414, filed on Nov. 18, 2011, the contents of which are incorporated herein by reference.

BACKGROUND

Molecular imaging has great promise for improving diagnosis and treatment of patients with various diseases. For example, PET/CT (PET—Positron Emission Tomography combined with CT Computerized Tomography scans utilizing injections of F-18 labeled tracer molecules to detect minute anomalies in the patients tissues. To assess the patient's response to treatment or predict whether a particular tumor will respond to a particular treatment, quantifying the behavior of the tissues, diseases, biological, or physiological under study could be necessary. Quantification is currently done in several ways:

In the standard uptake value (SUV) method, the tracer imaged in a tissue is normalized by the dose given and some patient characteristic, such as weight, lean body mass, or body surface area. However, SUV changes with the time between injection and image acquisition for different tumors.

Methods in which the patient is injected on the PET scanner and a series of images are acquired for 10 or 20 minutes and then 55 to 60 minutes post injection have provided some improvement over SUV. However, patient body position re-registration and patient waiting time between scans and logistics of rescanning pose problems with these methods. Acceptable results (80% correlation) have also been obtained using a 16 minute dynamic scan.

Thirty and 40 minute scans have been used to produce a model of the forward and reverse transport of FDG between the blood and tissue. However, these methods may be sensitive to the early phases of time-activity curves of tumor and input function.

Methods such as the Patlak plot, the Sokolof method, and the Logan Plot acquire PK/PD (pharmacokinetic/pharmacodynamic) by injecting the patient in the PET/CT scanner and acquiring images over a length of time. Models associated with these methods can calculate, estimate, or infer quantities such as tissue perfusion, blood vessel permeability, tissue glucose metabolism, and the presence of hypoxia. However, this often requires that the patient be in the scanner for 60 or 90 minutes.

DESCRIPTION OF DRAWINGS

In the following detailed description, reference is made to the accompanying drawings, which form a part hereof. In the drawings, similar symbols typically identify similar components unless context dictates otherwise. The illustrative embodiments described in the detailed description, drawings, and claims are not meant to be limiting. Other embodiments may be utilized and other changes may be made, without departing from the spirit or scope of the subject matter presented herein. It will be readily understood that the aspects of the present disclosure, as generally described herein and illustrated in the Figures, can be arranged, substituted, combined, separated, and designed in a wide variety of different configurations, all of which are explicitly contemplated herein.

FIG. 4 includes one exemplary method of the invention. FIG. 4a is a flow chart, FIG. 4b is a fluid path diagram, and FIG. 4c is an injector program table.

FIG. 5 includes graphs showing two-hand delivery of a tracer.

DETAILED DESCRIPTION

Figure 1:
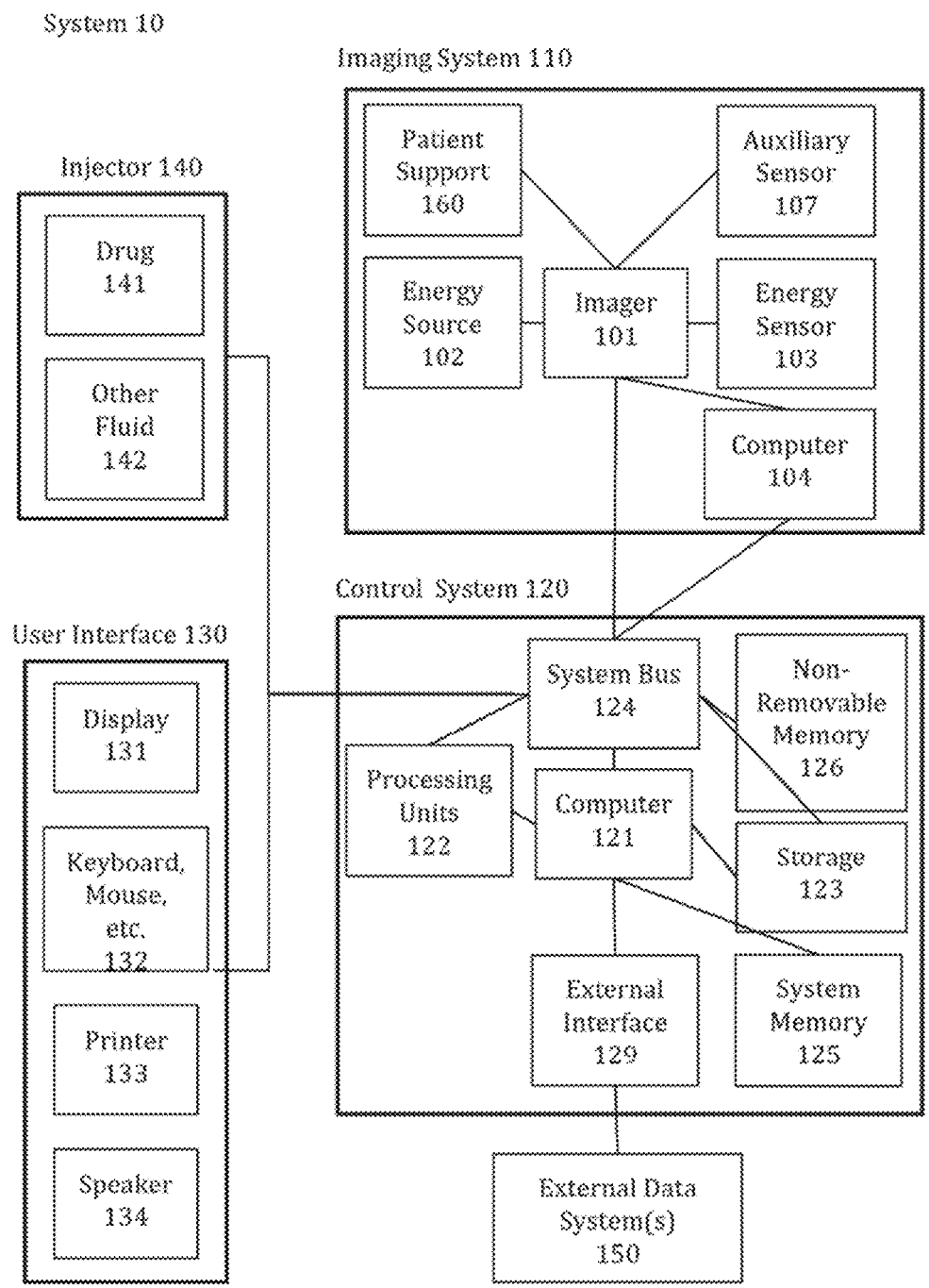
FIG. 1 is a flow chart representing the system of various embodiments.

The above summary of the present invention is not intended to describe each illustrated embodiment or every possible implementation of the present invention. The detailed description, which follows, particularly exemplifies these embodiments.

Before the present compositions and methods are described, it is to be understood that they are not limited to the particular compositions, methodologies or protocols described, as these may vary. It is also to be understood that the terminology used in the description is for the purpose of describing the particular versions or embodiments only, and is not intended to limit their scope which will be limited only by the appended claims.

It must also be noted that as used herein and in the appended claims, the singular forms "a," "an," and "the" include plural reference unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

"Optional" or "optionally" means that the subsequently described event or circumstance may or may not occur, and that the description includes instances where the event occurs and instances where it does not.

"Substantially no" means that the subsequently described event may occur at most about less than 10% of the time or the subsequently described component may be at most about less than 10% of the total composition, in some embodiments, and in others, at most about less than 5%, and in still others at most about less than 1%.

For purposes of the description hereinafter, the terms "upper," "lower," "right," "left," "vertical," "horizontal," "top," "bottom," "lateral," "longitudinal," and derivatives thereof shall relate to the orientation of embodiments disclosed in the drawing figures. However, it is to be understood that embodiments may assume alternative variations and step sequences, except where expressly specified to the contrary. It is also to be understood that the specific devices and processes illustrated in the attached drawings, and described in the following specification, are simply exemplary embodiments. Hence, specific dimensions and other physical characteristics related to the embodiments disclosed herein are not to be considered as limiting.

It is to be understood that the disclosed embodiments may assume various alternative variations and step sequences, except where expressly specified to the contrary. It is also to be understood that the specific devices and processes illustrated in the attached drawings, and described in the following specification, are simply exemplary embodiments. For example, where it is said that a parameter or data is derived from the image, it should be recognized that the measured data can be operated on in many ways to achieve the desired output or measurement, some of which use an intermediate image and others of which do not.

Various embodiments of the invention are directed to a system and methods for acquiring imaging data and providing improved pharmacokinetic (PK) and pharmacodynamic (PD) data. In general, such methods include the step of determining an input function from an organ or other part of a patient's body having a high blood volume and, in some embodiments, the input function may be determined two or more times throughout a procedure. In certain embodiments, the imaging data collected from the sample tissue can be normalized based on multiple input functions determined throughout the procedure, and the uptake of the tracer and diffusion or circulation of the tracer through the target organ can be more accurately assessed. Further embodiments, include systems for carrying out such methods that include injectors that are capable of providing controlled and continuous or repeated injection of the tracer throughout the procedure.

The imaging system of various embodiments as illustrated in FIG. 1 optionally uses a multi-compartmental physiological modeling convention for the tissue within a voxel (volume element). The blood consisting of plasma and cells, most prominently red blood cells, flows throughout the body, with different flow rates and different circulation times to each voxel or volume element in the body. Drugs including radioactive tracers used in imaging procedures are generally injected into the peripheral venous circulation with some injection profile. Each voxel of tissue usually contains some amount of blood contained within the intravascular space. The extravascular space generally includes extravascular fluids, a connective tissue matrix of some type, and cells, which have an intracellular space and have various metabolic activities occurring. Each voxel may also contain more than one material or tissue type, each with different properties, for example at the boundary of the lungs and rib cage which could have air, lung tissue, bone and muscle. Imaging systems measure energy that has been affected by the voxels. For example, imaging systems measure gamma rays emitted from the voxel in nuclear medicine, X-ray absorption in CT or angiography, a magnetic resonance property in MR, ultrasound reflectance or absorbance in ultrasound, light in optical or fluorescence imaging, sound in photoacoustic imaging, and other forms of energy in other imaging modalities. The measured energy is then processed and commonly represented as an image.

Physiological compartmental modeling is also called PK or PK/PD modeling. Pharmacokinetics (PK) may be simply defined as what the body does to the drug, as opposed to pharmacodynamics (PD), which may be defined as what the drug does to the body. It can be understood as creating a model for a voxel or region/volume of interest consisting of multiple voxels and fitting parameters in that model to a time series of data, measured, for example, by the imaging system 110.

In imaging procedures where PK/PD modeling is performed, an "input function" that represents the concentration of a tracer in the blood plasma over time must be determined for the model. Generally, diffusion of the tracer from the plasma into and out of the tissues of a target organ is modeled during or after imaging. Currently, to assess plasma concentration of a tracer, blood is drawn from an artery or an arterialized venous site, and the concentration of tracer, i.e., the input function, is determined based on the blood sample. However, many drugs diffuse into red blood cells with time constants on the order of seconds to minutes, and, diffusion out of the plasma occurs as the sample is being processed. And sampling of a patient's blood is difficult and inconvenient for both the patient and the health care workers. Therefore, convenience and accuracy of the input function determination can be improved by deriving the input function directly from the image, preferably with no blood sampling. Additionally, a whole blood to plasma curve as a function of time approach may be used, and patient specific information such as hematocrit may be incorporated into the model. The methods and systems described herein allow provide such improvements over current practices.

The methods of various embodiments of the invention include the step of determining an input function at least two times during an imaging procedure. An input function can be any normalizing parameter. For example, in some embodiments, the input function may be the amount of a particular compound such as a tracer in a sample of the patient's blood, or the amount of radioactive emissions from the sample, the amount of light emitted, or any combination thereof. Determining an input function can be carried out by any means known in the art. For example, in some embodiments, the tracer may be a radiopharmaceutical, and the input function may be the radioactive emissions from a blood sample from a patient who has been administered the radiopharmaceutical. In other embodiments, the input function may be determined based on the amount of radiopharmaceutical detected in a particular tissue or organ of the patient based on an image acquired after administration. In particular embodiments, the input function may be determined based on the amount of radiopharmaceutical detected in an organ having a high blood volume such as, for example, the heart, aorta, or ventricle, and the detecting may be carried out using an image of the high blood volume organ.

The amount of tracer can be based on the actual emission from the sample. For example, a light meter or camera may be used to determine the amount of a light emitting or fluorescent tracer. The amount of radioactive tracer such as a radiopharmaceutical can be determined using, for example, a Geiger counter, sodium iodide detector, multichannel analyzer, ionization (ion) chamber, neutron REM meter, scintillation counter, multichannel analyzer, and the like. In certain embodiments, the amount of tracer, including either light or fluorescence emitting tracer or radioactive tracer can be determined based on images acquired from the patient by, for example, determining the brightness of one or more pixels associated with the tissue or organ used to measure the input function such as, for example, the heart, aorta, left ventricle, or combinations thereof.

In some embodiments, the method may include the step of identifying the maximum blood concentration of the tracer before acquiring an image of the tissue or organ. Identifying the maximum blood concentration of the tracer can be carried out by injecting the tracer into the blood stream of the patient and monitoring the emissions in a particular tissue or organ until the amount of emission is constant for a period of time. For example, in some embodiments, a radiopharmaceutical may be administered to a patient and a first sample may be obtained from the patient a first time period after administration. A second sample may be obtained after a second time period after administration, and the emission data obtained from the first sample and second sample can be compared. Additional samples may then be obtained and compared to the first and second samples as well as all of the additional samples obtained. The step of obtaining additional samples can be repeated any number of times, and the number of times the step of obtaining additional sample is repeated can vary based on the procedure and the patient. For example, in some embodiments, the step of obtaining additional samples can be carried out until the sample immediately preceding and immediately following a particular sample are about equal and/or fall within a particular threshold such as, for example, about 2% difference, about 5% difference, about 10% difference, about 20% difference, and the like or any percent difference between these values. In further embodiments, more than the immediately preceding and immediately following samples may be accounted for in determining whether the maximum or desired blood value has been reached. In some embodiments, the first time period, the second time period, and each of the time periods between additional samples may be the same, and these time periods may be any time suitable period. For example, a first sample may be taken 30 seconds, 1 minute, 2 minutes, 5 minutes, 10 minutes, 15 minutes, 20 minutes, or the like and any time period between these exemplary time period. The second sample may be taken at the same time period as the first, and each additional sample can be taken after the same amount of time as elapsed. In other embodiments, the first time period may be longer than later time period. For example, the first sample may be taken 5 minutes after administration and the second and additional samples may be taken every 30 seconds thereafter. As discussed above, the term "sample" as used in the above description and below can refer to a physical sample such as, for example, blood drawn from the patient, or an estimate of the tracer concentration based on the brightness of pixels in an image associated with tissue under study or located in a high blood volume tissue or organ.

In certain embodiments, methods may include repeating the step of determining the input function during the procedure, and determining the input function can be repeated any number of times. For example, in some embodiments, the method may include the steps of identifying the maximum blood concentration, determining the input function after the maximum blood concentration has been reached, imaging a target organ or tissue, determining an input function, and reimaging the target organ or tissue. The steps of determining an input function and reimaging the target organ or tissue can be repeated any number of times.

Although the goal of this invention is to make the quantitative imagining procedure as short as possible, not all physiological phenomena have rapid time constants, so generally, the methods described above can be carried out for any amount of time provided the tracer is still observable in the images obtained, and because the images can be normalized, images taken after considerable tracer decay may still provide useable data. For a single a tracer administration, such a time period may be about 1 hour or about 2 hours. In certain embodiments, the method may further include administration of additional doses of a tracer. Additional doses of tracer can be administered at any time during the procedure, and because determining an input function and reimaging the target organ or tissue is repeated during the procedure, images obtained after the additional administration can be normalized to be consistent with images obtained prior to or during the additional administration. In certain embodiments, the additional administration may be carried out after a particular amount of decay has occurred. For example, readministering the tracer can be carried out after a 40%, 50%, 60%, 70%, 80%, or 90% reduction in emission detection is observed in the input function as compared to the input function at maximum blood value. Readministration may be determined manually, or in other embodiments in which a system, such as that described below, is used to administer the tracer, image the target organ, and normalize the images based on the input functions determined over time, readministration can be carried out automatically using, for example, an injector. Because readministration can be carried out numerous times throughout the procedure using the method of embodiments, the procedure can be carried out, and normalized images can be obtained of the patient, for any amount of time from several hours to several days or several weeks.

Some embodiments are directed to a system designed to carry out the methods described above. The complexity of such systems may vary depending on the amount of automation incorporated into the system. For example, the methods above can be carried out by manually injecting the tracer and determining the input function, imaging the target tissue or organ, and normalizing the images using an imager operably connected to a computer. More automated systems may include the components illustrated in FIG. 1.

FIG. 1 shows an exemplary embodiment of an imaging and analysis system 10 of the invention. In various embodiments, the system may include an imaging system 110 configured to image a patient. In some embodiments, the imager system 110 may include an imager 101 that has an energy source 102 configured to transmit energy into a patient and an energy sensor 103 that collects energy from the patient and converts energy received over time into a stream of data that can be transferred to and collected by a control system 120, or a computer 104 associated specifically with the imaging system 110, that is capable of interpreting and manipulating the data and displaying an image on a display 131 associated with a user interface 130. The energy can be transmitted through the patient or reflected, scattered, or otherwise interact with the patient or the drug given to the patient. A sensor 103 associated with the imaging system can be positioned to receive either transmitted or reflected/scattered energy and use the received energy to produce data that can be used to produce an image of the patient. The energy source may generally be an integral part of the imaging system; however, in some embodiments, the energy source may be the patient himself in, for example, black body radiation. In several embodiments of this invention, the energy source 102 is the drug or tracer 141 which contains a radioactive atom. Exemplary imaging systems 110 that can be incorporated into the system 10 of various embodiments include, but are not limited to, positron emission tomography (PET) imagers, computed tomography (CT) imagers, magnetic resonance imaging (MR) imagers, single-photon emission computed tomography (SPECT) imagers, and combinations thereof including, for example, PET/CT imagers, PET/MR imagers, SPECT/CT imagers, and the like.

The data or information acquired by the imaging system 110 can be transmitted to a control system 120 that can include various components necessary to compile data acquired from the imager 101, analyze the data, and transmit the data to an output device in a user accessible format. The control system may include one or more computers 121 or similar computing devices having a computer-readable storage medium 123 capable of storing computer-readable program code or instructions that cause the processing unit 122 to execute, configure, or otherwise implement the methods, processes, and transformational data manipulations necessary to carry out the methods described above. The computer 121 can include one or more processing units 122 (typically referred to as a central processing unit or CPU) that serves to execute computer-based instructions received in the appropriate data form and format. In some embodiments, the processing unit 122 can be in the form of multiple processors executing code in series, in parallel, or in any other manner for appropriate implementation of the computer-based instructions. In various embodiments, the computer 121 may be operably configured to execute appropriate software to perform and implement the processing steps of the methods described above. The computer 121 may be in the form of a personal computer coupled to the system 10, a processor formed integrally with the imaging system 110, a computer separate from the imaging system 110, or any other type of computing device having the necessary processing hardware to appropriately process data to effectively implement the methods described above.

The control system 120 may further include a system bus 124 to facilitate appropriate data communication and processing information between the various components of the computer 121. The system bus 124 may be any of several types of bus structures, including a memory bus or memory controller, a peripheral bus, or a local bus using any of a variety of bus architectures. In particular embodiments, the system bus 124 may facilitate data and information communication between the various components (whether internal or external to the computer 121) through interfaces.

In some embodiments, the computer 121 may include one or more discrete computer-readable media components that can be contained on the computer-readable storage medium 123. The computer-readable storage medium 123 may be any method or technology for storage of information such as computer-readable instructions, data structures, program modules, or other data, including, but not limited to, random access memory (RAM), read only memory (ROM), electrically erasable programmable read only memory (EEPROM), flash memory, or other memory technology, CD-ROM, digital versatile disks (DVDs), or other optical disk storage, magnetic cassettes, magnetic tape, magnetic disk storage, or other magnetic storage devices, or any other medium which can be used to store the desired information and which can be accessed by the computer 121. The computer-readable media contained on the computer readable storage medium 123 may include any media that can be accessed by the computer 121, such as volatile media, non-volatile media, removable media, non-removable media, and the like. In some embodiments, the computer-readable media may include communications media, such as computer-readable instructions, data structures, program modules, or other data in a modulated data signal such as a carrier wave, or other transport mechanism. In other embodiments, the computer-readable media may include any information delivery media, wired media (such as a wired network and a direct-wired connection), and wireless media (such as acoustic signals, radio frequency signals, optical signals, infrared signals, biometric signals, bar code signals, etc.). Combinations of any of the above are also included within the scope of computer-readable media.

In still other embodiments, the computer 121 may further include system memory 125 such as volatile and non-volatile memory, ROM, and/or RAM. A basic input/output system (BIOS) with appropriate computer-based routines assists in transferring information between components within the computer 121 and can be stored in ROM. The RAM portion of the system memory 125 typically contains data and program modules that are immediately accessible to or presently being operated on by processing unit 122 such as, for example, an operating system, application programming interfaces, application programs, program modules, program data, and other instruction-based computer-readable code.

The computer 121 may also include other removable or non-removable, volatile or non-volatile computer storage media products. For example, the computer 121 may include a non-removable memory 126 that includes a non-removable, non-volatile magnetic medium, a removable, non-volatile memory interface that communicates with and controls a magnetic disk drive unit that reads from and writes to a removable, non-volatile magnetic disk, an optical disk drive unit that reads from and writes to a removable, non-volatile optical disk, such as a CD ROM, a Universal Serial Bus (USB) port for use in connection with, for example, a removable memory card, and the like and combinations thereof. Other removable or non-removable, volatile or non-volatile computer storage media can be used in the exemplary control system 120, including, but not limited to, magnetic tape cassettes, DVDs, digital video tape, solid state RAM, solid state ROM, and the like. These removable or non-removable, volatile or non-volatile magnetic media can be configured to be in communication with the at least one processing unit 122 and other components of the computer 121 via the system bus 124. The drives and their associated computer storage media discussed above provide storage of operating systems, computer-readable instructions, application programs, data structures, program modules, program data, and other instruction-based computer-readable code for the computer 121 whether duplicative or not of the information and data in the system memory 125.

The system 10 may include one or more user interfaces 130 associated with the controller system 120. The user interface may include one or more displays 131 or graphical user interfaces (GUI) that are capable of displaying images and other graphics in color or black and white and configured to present or provide data and information to an operator in an intelligible form or format. In some embodiments, the display 131 may be configured to allow a user to program or otherwise operate the system 10, and in various embodiments, the display 131 may display real-time data with regard to the operation of the system. For example, in certain embodiments, the display 131 may have touch-screen capabilities or be otherwise configured to allow a user to interact with the control system 120 and, in particular, the computer 121 associated with the control system, by manipulating or touching the display 131. In other embodiments, the system user interface 130 may include a keyboard, mouse, or other device 132 configured to allow the user to program or otherwise operate the system.

In particular embodiments, the display 131 may be included as part of a laptop or tablet computer that is electronically associated to the system by a hard wired or wireless network. In other embodiments, the display 131 may be fixed to the system via a housing that encompasses the imaging system 110 and the control system 120. Such displays 131 may be configured to be tilted or swiveled to allow the display 131 to be positioned by an operator. In further embodiments, the display 131 may be positioned away from the system and attached to the system by a hard wired or wireless network.

In certain embodiments, the system 10 may include a printer 133 that is configured to physically display this information and data in print form. The printer of various embodiments may be of any type and includes off the shelf ink-jet and laser printers. In particular embodiments, the printer may be configured to print adhesive backed labels. In still other embodiments, the system 10 may include a speaker 134 to audibly present this information and data in audible form. For example, a speaker may be configured to produce an audible "beep" when the method or a portion of the method is complete. For example, the system may be configured to provide a "beep" when maximum blood value has been reached or when the input function has reached upper or lower thresholds. In various embodiments, such devices may be in communication with the computer or other control system through output interfaces.

In particular embodiments, the system 10 may be configured to allow a user to enter commands, information, and data into the computer 121 using the touch-screen of the GUI display 131 via an user interface 130. However, it has been envisioned that an operator may enter commands, information, and data into the computer 121 using other attachable or operable input devices, such as a keyboard, a mouse, a remote control device, a microphone, a trackball, a joystick, a touchpad, a scanner, a tablet computer, and the like, via the user interface 130. Any arrangement that facilitates the input of data and information to the computer 121 from an outside source may be used including, for example, hard wiring or accessing using a wireless network device, such as blue tooth, a wireless internet connection, or a cellular connection. As discussed, these and other input devices are often connected to the control system 120 through the user interface 130 coupled to the system bus 124, but may be connected by other interface and bus structures, such as a parallel port, game port, or a USB.

The display 131 may provide output image that are single plane representations of a 3D voxel data set or 3D graphical images. In some embodiments, the output image may provide all the data presented to the user. In other embodiments, the output image may further provide various physiologically relevant parameters such as blood volume, blood flow, drug uptake or diffusion, drug metabolism that can provide information to the user that can be used, for example, in diagnosis of a patient's condition.

In certain embodiments, the control system 120 will include and external interface 129 for communications of data into or out of system 10. The external interface 129 can connect to one or more other external data or computer systems 150 over any of a multitude of communications medium with their applicable communications protocols. The data coming in may include, for example, patient and procedure or protocol ordering or schedule information. Data going out can include DICOM data going to a PACS system, or information about the procedure to a hospital information systems (HIS) or radiology information system (RIS). Such information can be used for billing, safety, efficiency or a myriad of other uses.

Figure 6:
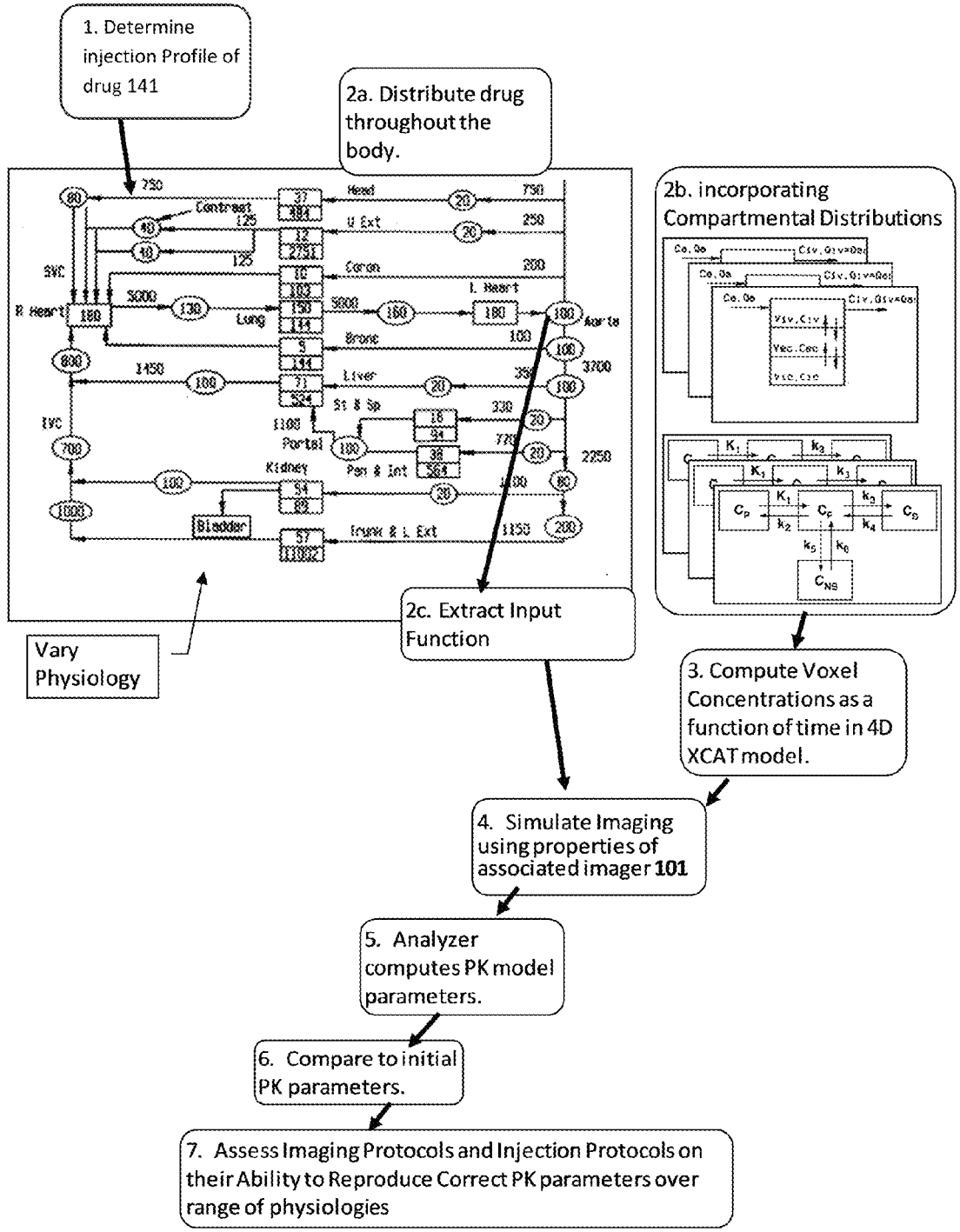
FIGS. 6a and 6b include a flow chart representation of the simulator.
Figure 6A:
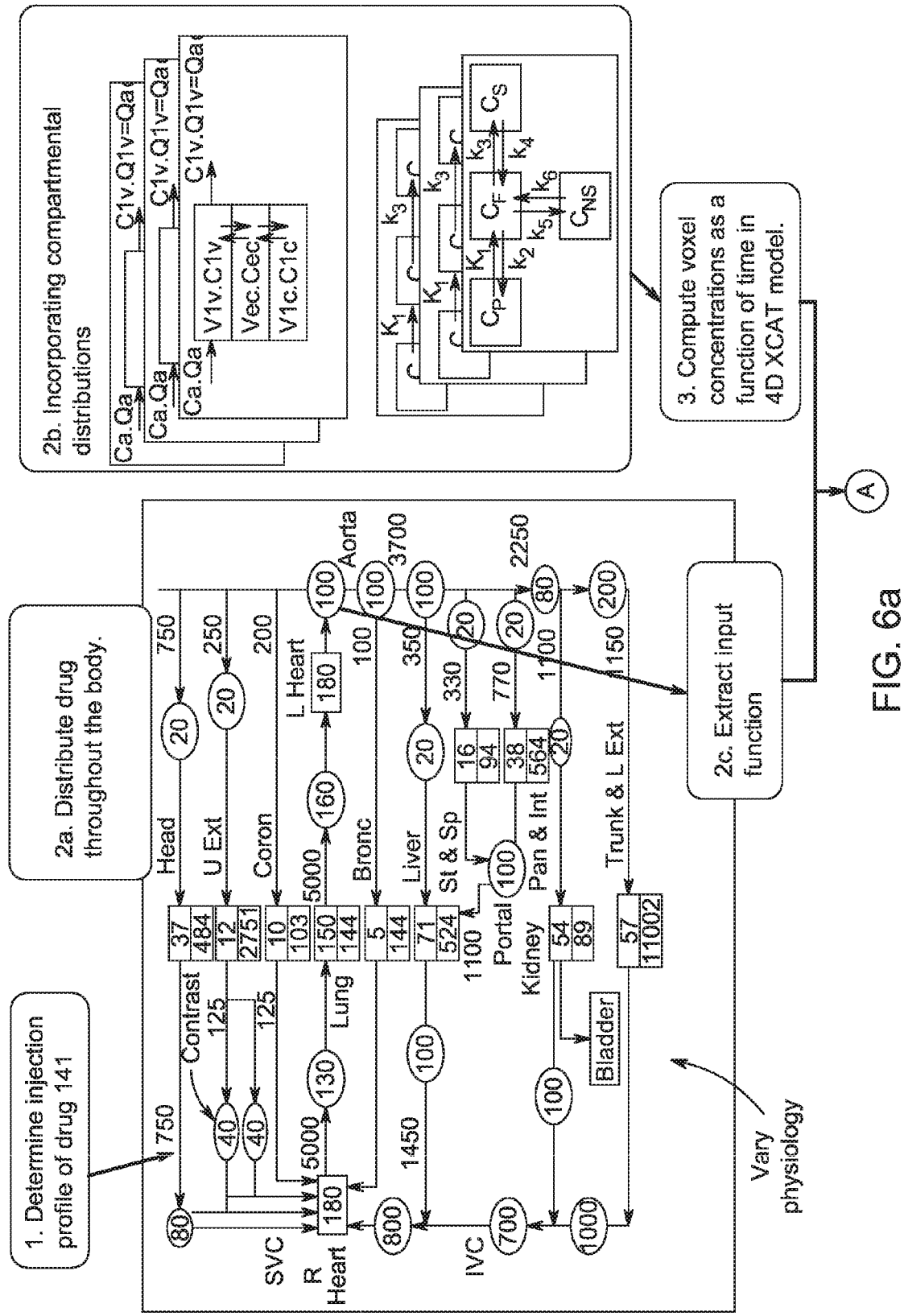
Figure 7A:
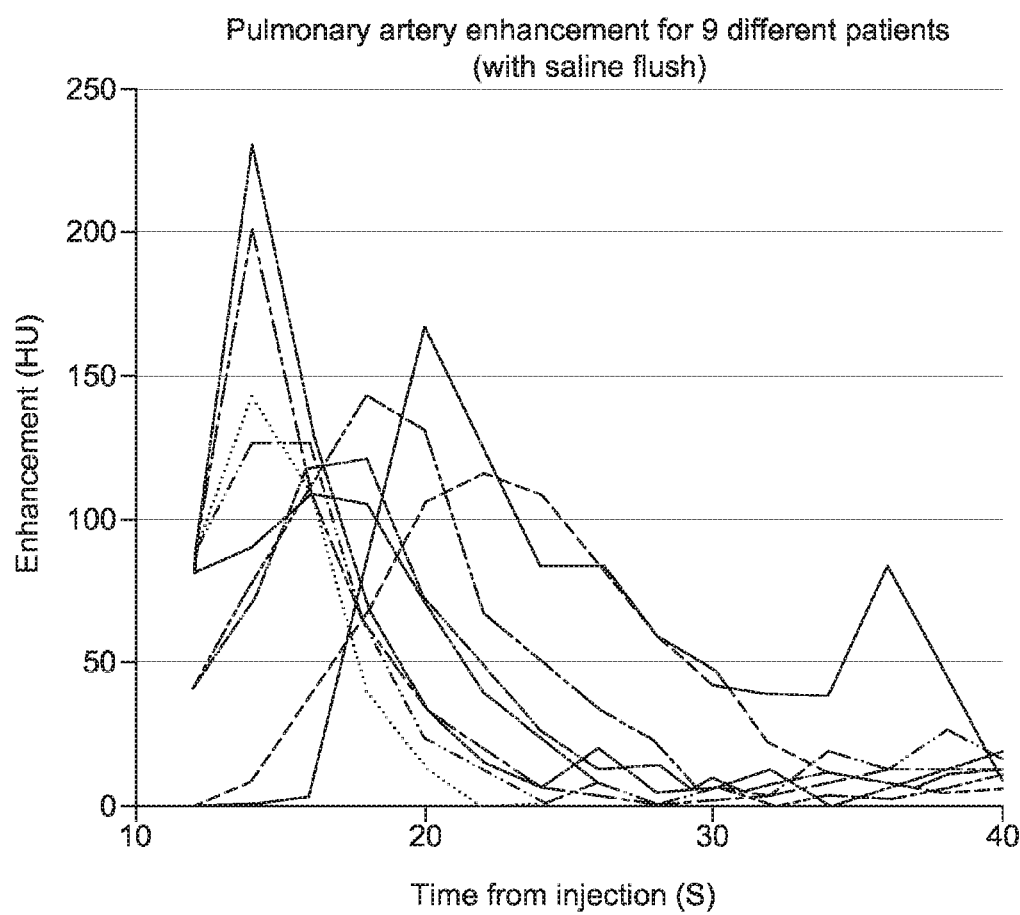
Figure 7B:
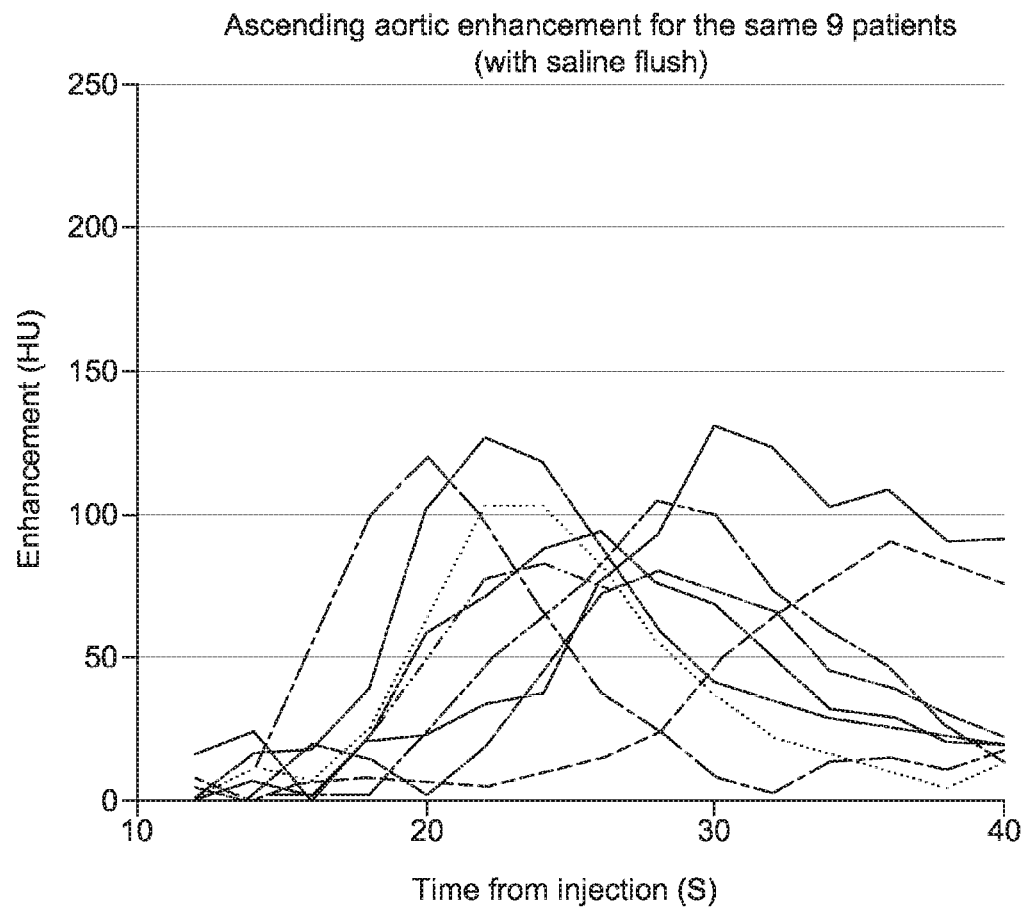
Figure 7C:
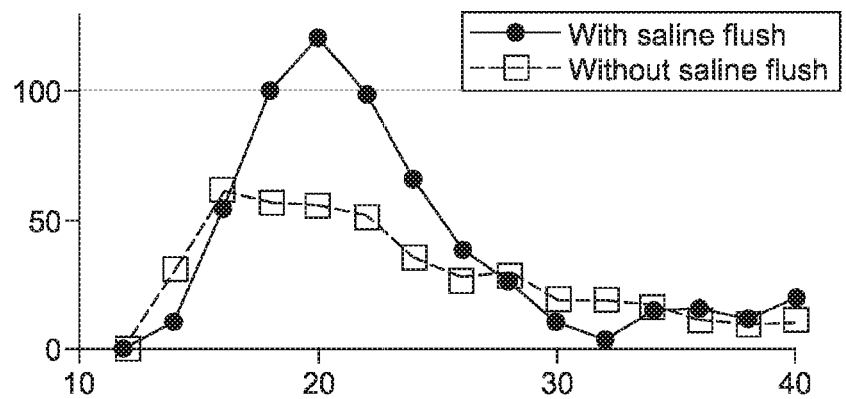
Figure 7D:
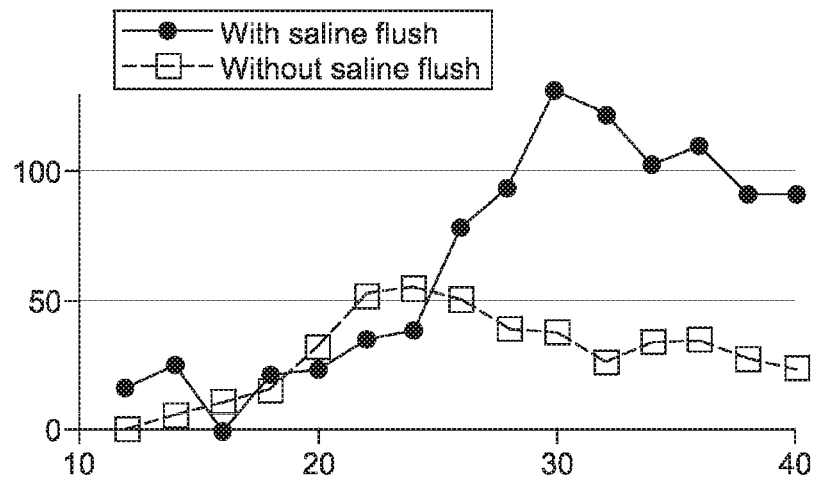
Figure 7E:
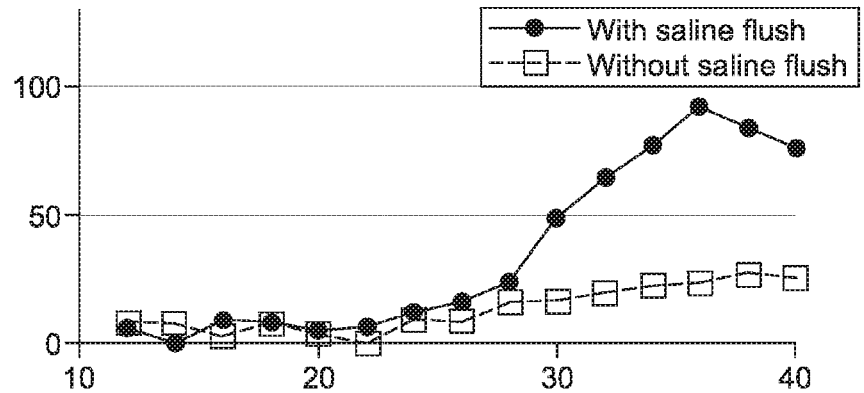

In certain embodiments, the computer 104 or 121 of system 10 may include a protocol simulator as illustrated in FIGS. 6a and 6b that is configured to simulate delivering the tracer, collecting the data, and analyzing the data. During simulation, patient circulation, uptake of the tracer by selected tissues, and excretion and degradation of the tracer can be simulated. The compartmental model operates within a physical 3D or 4D model of the body, so that tissue concentrations can be given a location in space. Such models have been developed for CT, PET, and SPECT image acquisition. These models allow iterative reconstruction methods to account for various sources of noise and distortion. Using the model with the known capabilities and limitations of imaging system 110, the simulator creates the data that would have been measured by the real imaging system 110 given the simulated distribution of the tracer. This data is then used by the control system 120, and a quantitative assessment and diagnosis can be made. Because the quantitative results come from a simulation, the results can be compared to the compartmental model parameter that went into the simulations to assess how well the proposed protocol would allow for identification of the correct compartmental properties. This simulator may not be used for every patient but can be used to assess and optimize imaging and drug delivery protocols for new drugs, new theories of disease, or when there is a significant deviation in some condition, such as patient weight, size, or another factor.

In some embodiments, a physician or other medical personnel may carry out injection of the tracer manually. In other embodiments, the system 10 may further include an injector 140 configured to inject or administer a tracer or drug 141 to a patient, and in some embodiments, the injector 140 may be further configured to inject or administer saline or other fluid 142 to a patient before, during, or after administration of the tracer 141. For example, in some embodiments, the injector 140 may simply inject one or more prescribed dosages of a tracer 141 directly into a patient's blood stream via a hypodermic needle and syringe. In other embodiments, the injector 140 may be configured to continually administer saline 142 to a patient through a peripheral IV line (PIV) and one or more prescribed dosages of the tracer 141 may be introduced into PIV and administered to the patient. In still other embodiments, the injector 140 may be configured to inject a dose of tracer 141 followed by administration of a particular volume of saline 142.

In some embodiments, the system 10 may be configured to administer a single tracer 141, and in other embodiments the system may be configured to deliver two or more different tracer. In embodiments in which the system is configured to deliver multiple tracers 141, the system may allow the operator to switch configurations depending on the intended procedure. The amount of each tracer 141 delivered by the system may vary among embodiments and based on the protocol being used. Generally, a physician or other qualified medical personnel can determine an appropriate amount of tracer 141 to be delivered to a particular patient using metrics regarding the patient known in the art. Because of the flexibility of the system, any amount of one or more tracers can be delivered. The injector may be configured to inject two or more tracers either individually, sequentially, or simultaneously. As such, in certain embodiments, the injector may include two or more reservoirs such as vials or syringes capable of holding a radiopharmaceutical prior to administration. The injector may further include additional medical fluid reservoirs capable of holding, for example, saline, other drugs, or other fluids.

The system 10 may be configured to deliver any tracer 141. For example, the systems of various embodiments may be configured to deliver any radiopharmaceutical known in the art alone or in combination with another pharmaceutical compositions. For example, in some embodiments, the system may be designed and configured to deliver $^{47}Ca$—$Ca^{2+}$, $^{11}$C-L-methyl-methionine, $^{14}$C-glycocholic acid, $^{14}$C-para-amino benzoic acid (PABA), $^{14}$C-urea, $^{14}$C-d-xylose, $^{51}$Cr-red blood cells, $^{51}$Cr—Cr$^{3+}$, $^{51}$Cr-ethylenediaminetetraacetic acid (EDTA), $^{57}$Co-cyanocobalamin (vitamin B$_{12}$), $^{58}$Co-cyanocobalamin (vitamin B$_{12}$), $^{169}$Er-colloid, $^{18}$F-fluorodeoxyglucose (FDG), $^{18}$F-fluoride, $^{18}$F-fluorocholine, $^{68}$Ga-dotatoc or dotatate, $^{3}$H-water, $^{111}$In-diethylenetri-aminepenta-acetic acid (DTPA), $^{111}$In-leukocytes, $^{111}$In-platelets, $^{111}$In-pentetreotide, $^{111}$In-octreotide, $^{123}$I-iodide, $^{123}$I-o-iodohippurate, $^{123}$I-m-iodobenzylguanidine (MIBG), $^{123}$I-FP-CIT, $^{125}$I-fibrinogen, $^{131}$I-iodide, $^{131}$I-iodide, $^{131}$I-m-iodobenzylguanidine (MIBG), $^{59}$Fe—Fe$^{2+}$ or Fe$^{3+}$, $^{81m}$Kr-aqueous, $^{13}$N-ammonia, $^{15}$O-water, $^{32}$P-phosphate, $^{82}$Rb-chloride, $^{153}$Sm-ethylenediaminotetramethylenephosphoric acid (EDTMP), $^{75}$Se-selenorcholesterol, $^{75}$Se-23-Seleno-25-homo-tauro-cholate (SeHCAT), $^{22}$Na—Na$^+$, $^{24}$Na—Na$^+$, $^{89}$Sr-chloride, $^{99m}$Tc-pertechnetate, $^{99m}$Tc-human albumin, $^{99m}$Tc-human albumin macroaggregates or microspheres, $^{99m}$Tc-phosphonates and phosphate, $^{99m}$Tc-diethylenetriaminepenta-acetic acid (DTPA), $^{99m}$Tc-dimercaptosuccinic acid (V) (DMSA), $^{99m}$Tc-dimercaptosuccinic acid (III) (DMSA), $^{99m}$Tc-colloid, $^{99m}$Tc-hepatic iminodiacetic acid (HIDA), $^{99m}$Tc-denatured red blood cells, $^{99m}$Tc-red blood cells, $^{99m}$Tc-mercaptoacetyltriglycine (MAG3), $^{99m}$Tc-exametazime, $^{99m}$Tc-sestamibi (MIBI-methoxy isobutyl isonitrile), $^{99m}$Tc-sulesomab (IMMU-MN3 murine Fab'-SH antigranulocyte monoclonal antibody fragments), $^{99m}$Tc-human immunoglobulin, $^{99m}$Tc-tetrofosmin, $^{99m}$Tc-ethyl cysteinate dimer (ECD), $^{201}$Tl—Tl$^+$, $^{133}$Xe in isotonic sodium chloride solution, $^{90}$Y-silicate, and the like and combinations thereof. In certain embodiments, the system may be configured to deliver $^{18}$F-fluorodeoxyglucose (FDG). Exemplary non-radioactive drugs include X-ray or CT contrast such as Ultravist® or Omnipaque™, MR contrasts such Gadovist®, as well as ultrasound contrasts and optical tracers.

The injector 140 in combination with the control system 120 can enable operation and synchronization of administration of the tracer or drug 141 for short events such as a seizure or a CT scan or longer events such as sustained levels of neurotransmitter for a brain study or other long time constant PK studies. It can provide patient specific profiles to achieve desired plasma or tissue levels of tracer 141. Generally, the injector 140 can provide a short tight bolus injection of a tracer 141 with or without saline or other fluid 142 flush for first pass or dynamic visualization of perfusion differences, in other embodiments, the injector may provide a slow injection of the tracer. For example, the system 10 may allow the user to program the injector 140 to inject a tracer 141 at a certain rate based on volume (ml), mass (mg), or activity (mCi) over time. Therefore, injection of, for example, a 30 ml dose of a radiopharmaceutical having an activity of 10 mCi can be carried out over, for example, 10 seconds, 20 seconds, 30 seconds, 45 seconds, 60 seconds, 90 seconds, 1 minute, 2 minutes, 3 minutes, 5 minutes, 10 minutes, 20 minutes, 30 minutes, 1 hour, or the so forth and any time period selected by the operator or user. The system 10 may also allow the user to program the injector 140 to inject several discrete doses of tracer over a period of time, for example, one 10 ml injection every 5 minutes or 10 minutes for 30 minutes or 40 minutes. The system 10 can further vary the injection based upon feedback about the condition of the patient based upon the measurements of the energy sensor 103 or an auxiliary sensor 107 associated with the imaging system 110. For example, a certain dose of tracer 141 may be administered when the input function reaches a particular lower threshold, or injection can be halted when an adverse event is observed or detected.

In some embodiments, the system may include auxiliary sensors 107 that track and monitor additional patient body functions during the imaging procedure. Such auxiliary sensors 107 are not limited and can include electro-cardiograms (ECG), respiration monitors, motion sensors, and the like and combinations thereof. In certain embodiments, the auxiliary sensors 107 may be configured to continuously monitor, for example, respiration, ECG, EEG, and/or other physiological indications of the physical state or status of the patient that can affect how the data collected is adjusted. For example, respiration moves the organs of the chest and abdomen in a repeatable way. ECG is synchronized with changes in heart wall position and wall thickness, which can affect the correct measurement of the image derived input function. In addition, motion correction or compensation is useful in the more accurate analysis of any voxel properties. Data acquired by the auxiliary sensors can be real time by the imaging system 110 and collected by a control system 120 and incorporated into the output provided to the user through the user interface 130.

In other embodiments, the system may include one or more patient supports or patient positioners 160 for maintaining patients in a constant known position during the scan. Normally no restraint is applied to the patient in PET imaging because dynamic scans are not routinely done in most clinical practices. Sometimes straps are used to make sure that the patient does not fall off of the imaging table or platform so that the patient feels secure. In some embodiments, sealed bags of polystyrene beads may be provided on the table or platform on which the patient lays that move and conform to the contours of the patient when at atmospheric pressure. When the air is removed from the bag, it becomes a relatively rigid brace thereby providing support for the patient while preventing or reducing patient motion. In other embodiments, the patient support 160 can quickly and accurately move the patient between scan or bed positions as the scan takes place ensuring that events detected by the energy sensor 103 are attributed to the correct voxel by the system controller 120 during analysis.

The controller system 120, injector 140, and imaging system 110 may all contain computer functions that may be performed by one or more computers. The manner in which the planning of the procedure, execution of the plan, and analysis of the data acquire is partitioned between the various components or devices of the total or overall system can vary depending upon the preference of the manufacturer or manufacturers. Generally, the control system 120 may collect data from each of the other components and the various computers associated with the injector 140 and imaging system 110, and coordinate activities of the system 10. For example, the system controller 120 may control and coordinate injection profiles (tracer and saline) that influence the input function of the tissue of interest, imager bed position sequence and timing, collimation, mode of acquisition (2D, 3D, TOF), slice duration, data capture (list mode, in some embodiments, for flexible reconstruction), PK/PD model used, ECG synchronization/acquisition, and the application of anatomical information from CT or MR, especially for example tissue boundaries to allow for significant changes in PK/PD model results.

The control system uses the data from the imaging system to first determine the input function and then to conduct the analysis determined by the operator. Among the more sophisticated analysis is a voxel by voxel, or at least a region of interest, multi-compartmental PK/PD analysis. Among the less sophisticated would be a Patlak analysis. The least sophisticated would be a simple SUV, preferably corrected for residual blood concentration.

Figure 7A:
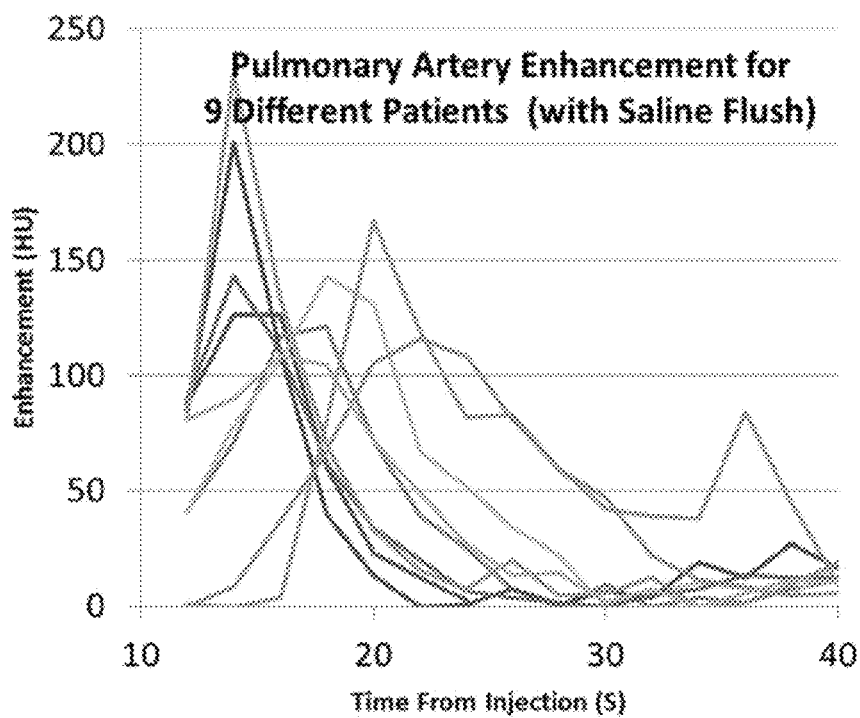
FIGS. 7a-7e include example data collected measured on patients.
Figure 7B:
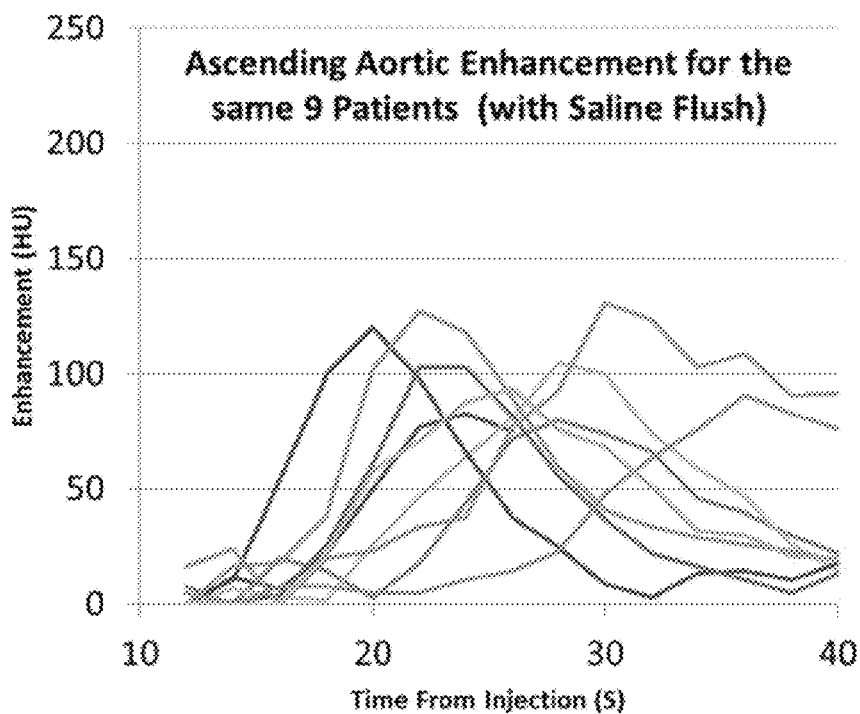
Figure 7C:
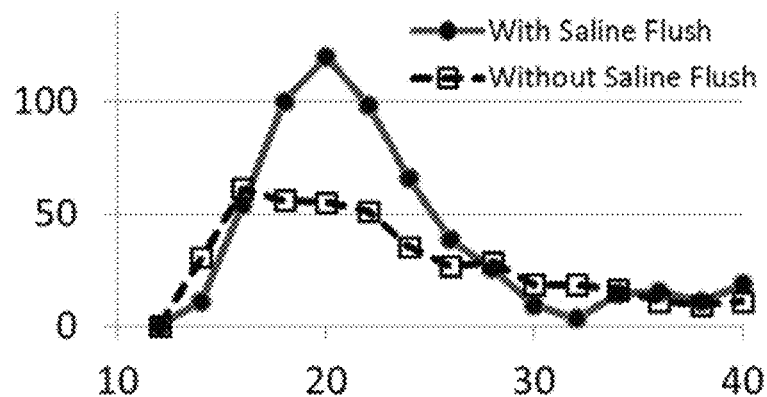
Figure 7D:
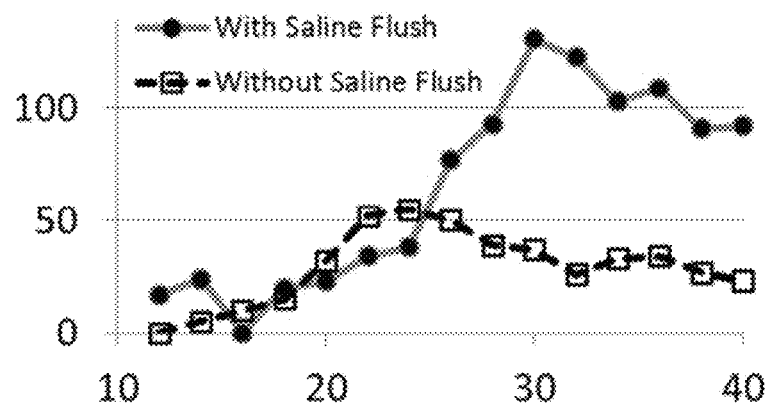
Figure 7E:
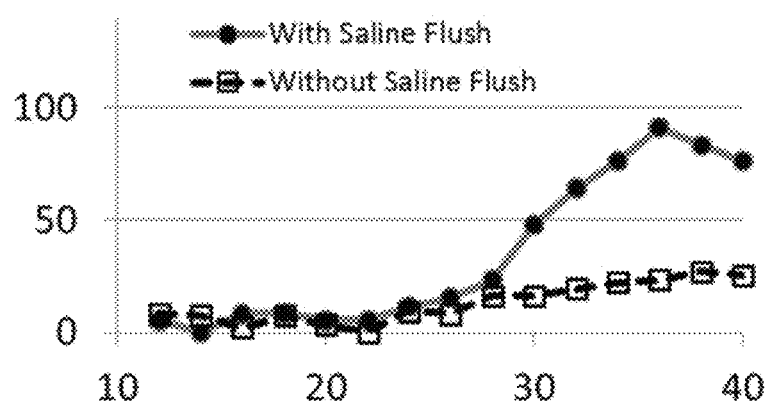
Figure 1:
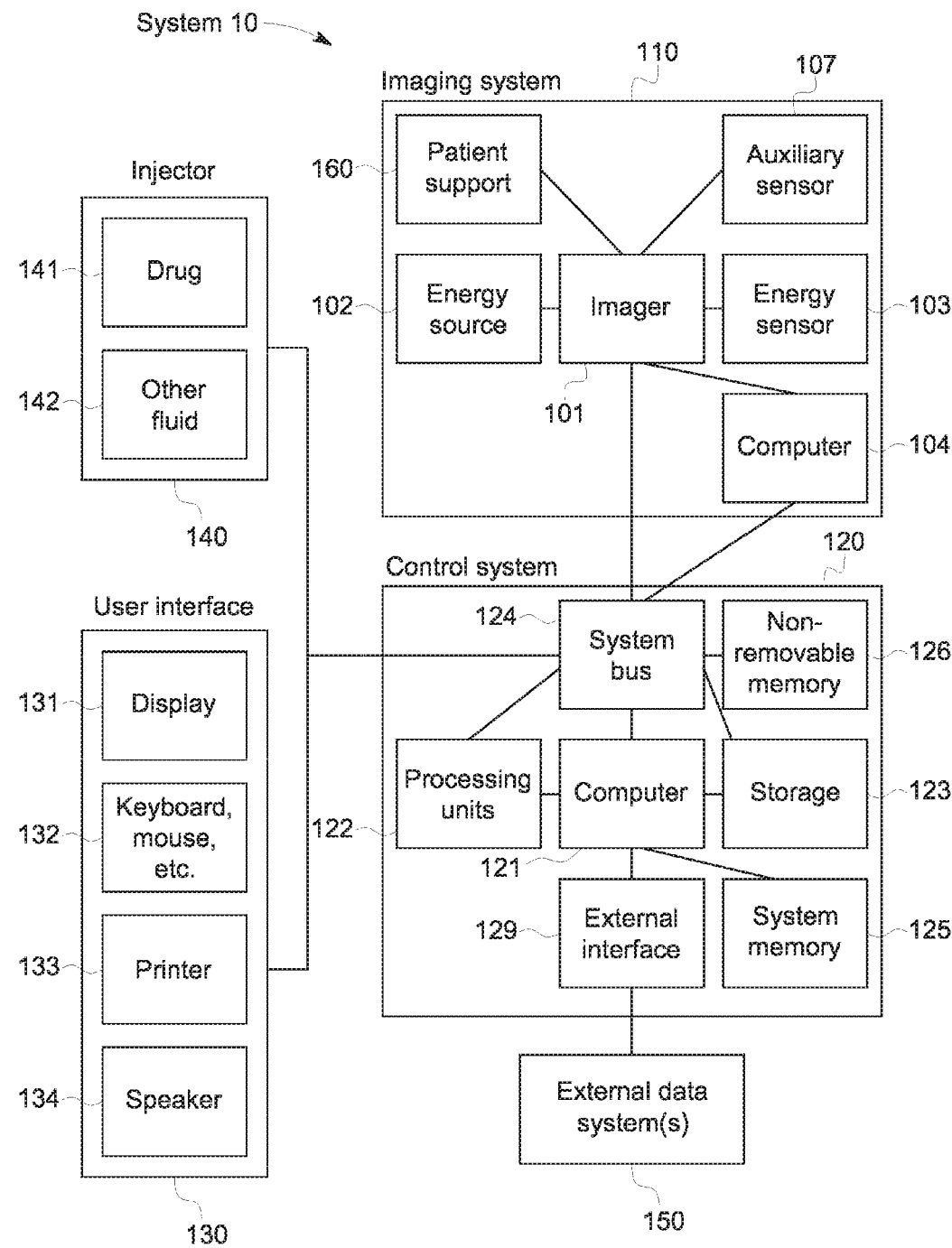
Figure 2:
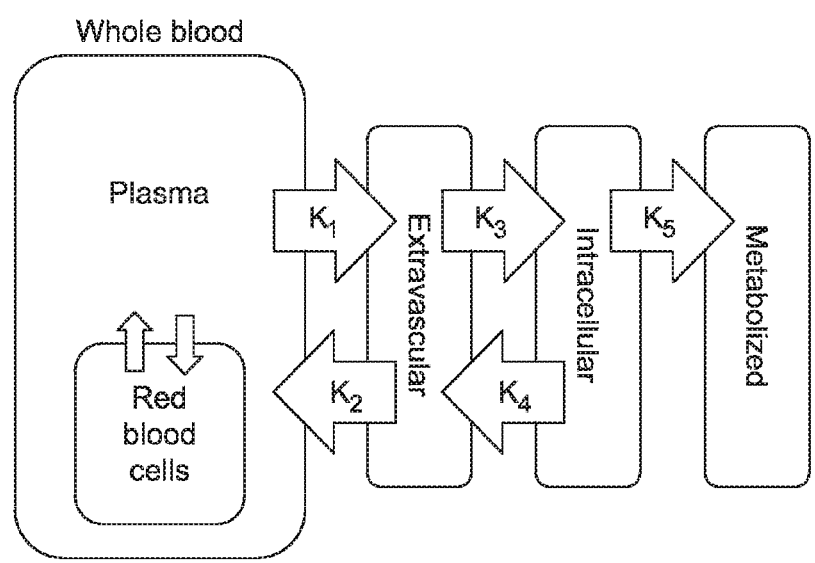
Figure 3A:
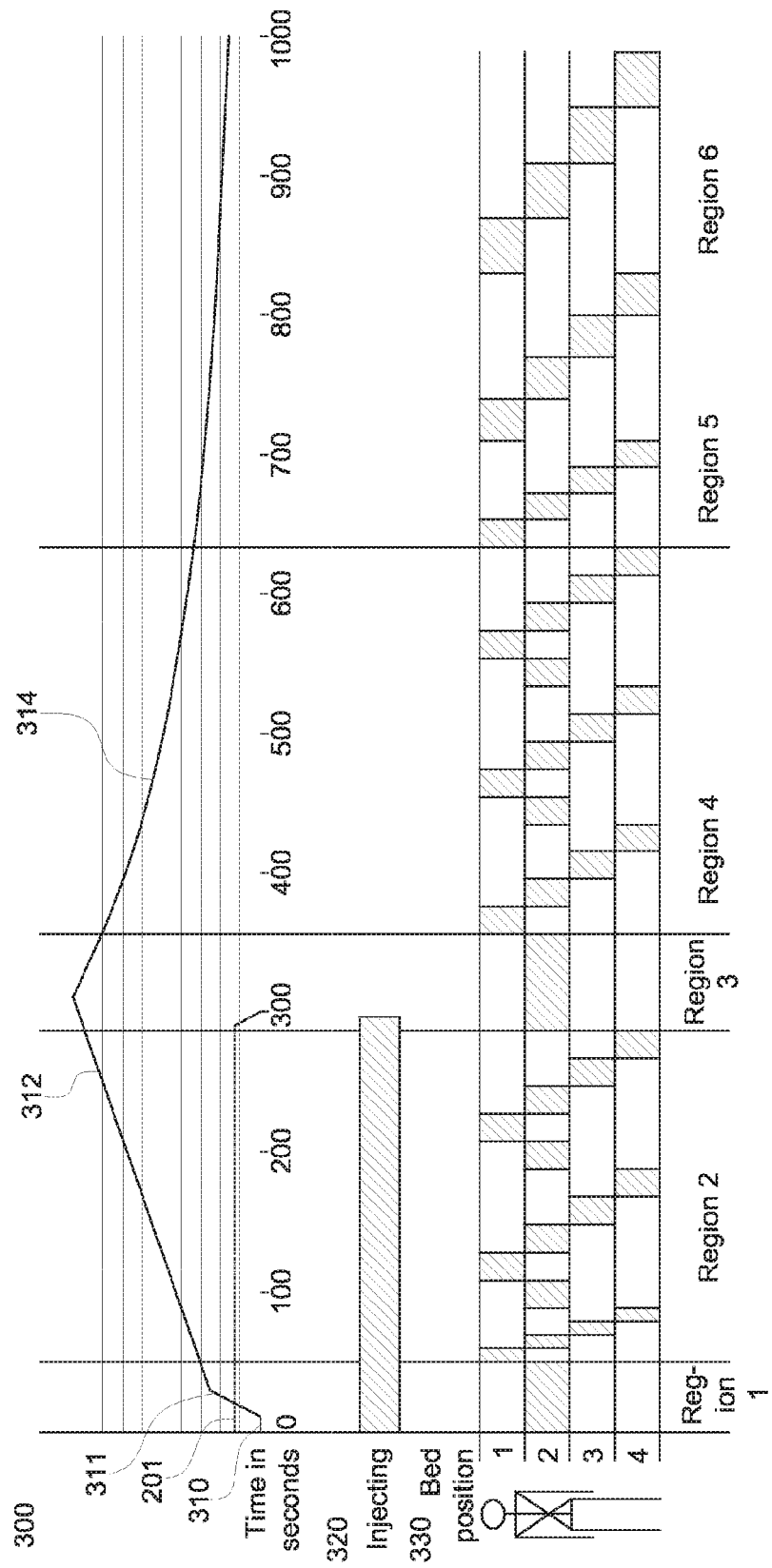
Figure 3B:
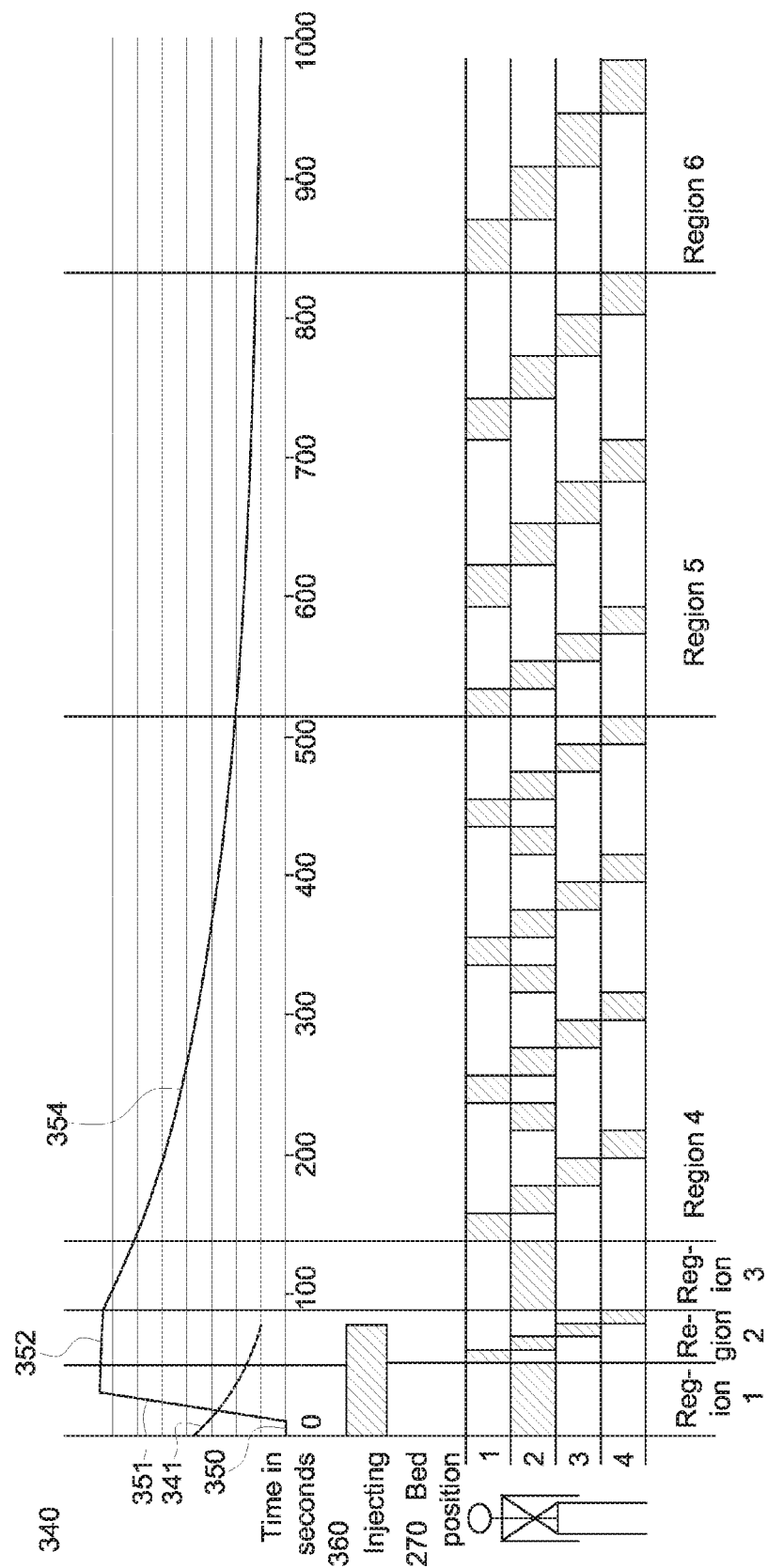
Figure 5A:
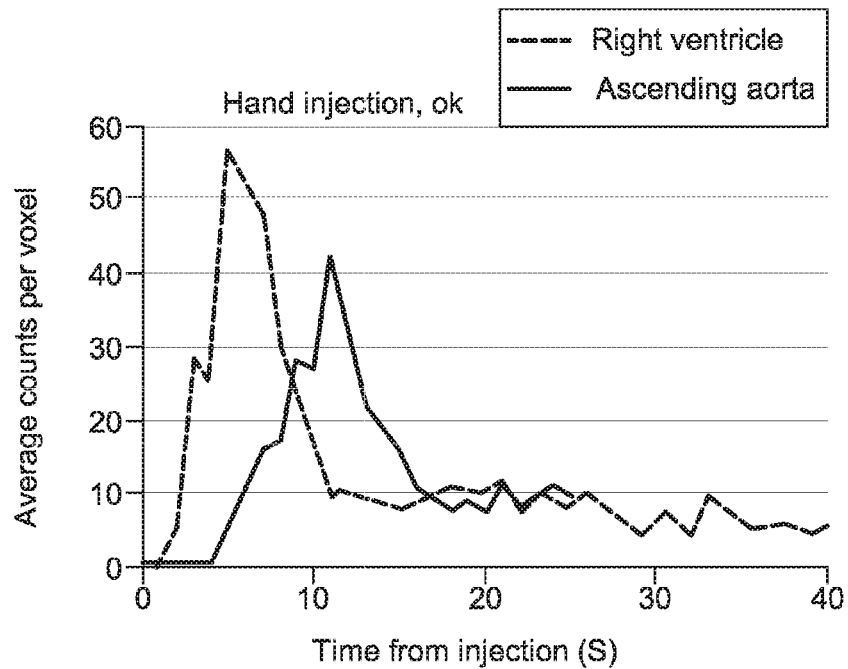
Figure 5B:
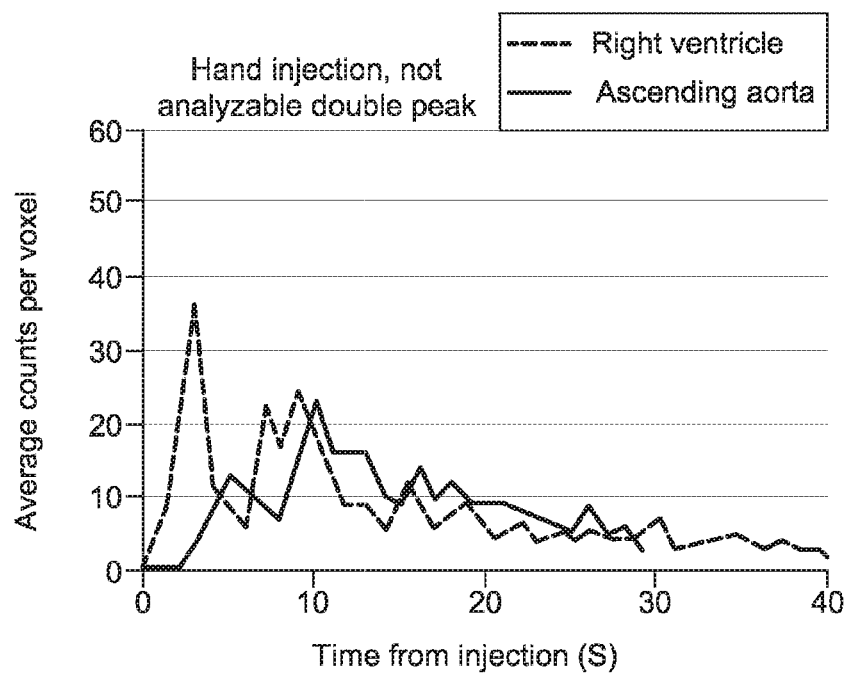
Figure 5C:
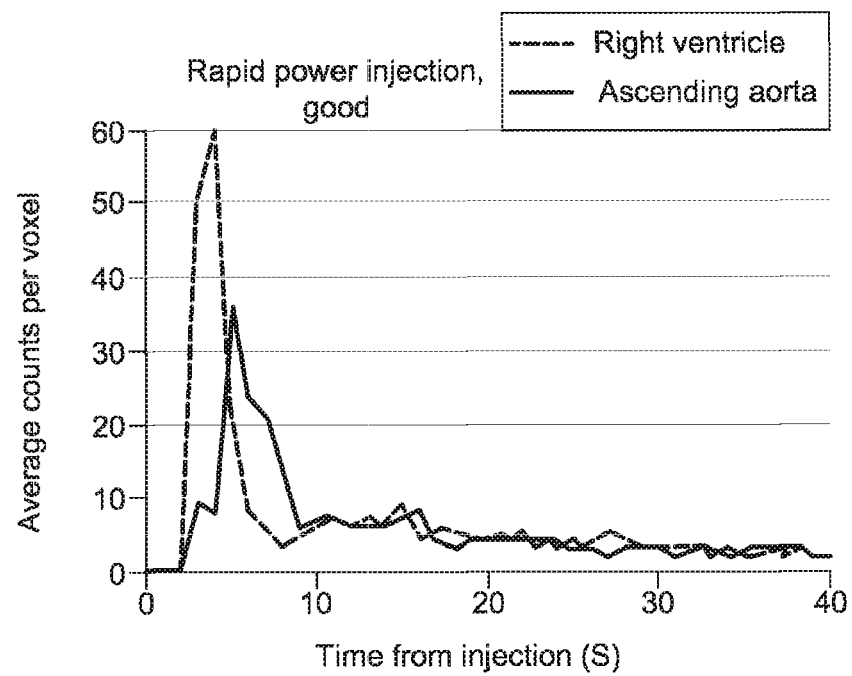

The system 10 can be configured to control, affect, measure, or account for various aspects of imaging procedures to more accurately determine PK/PD parameters and provide more accurate data for the user, doctor or other health care professional. For example, in various embodiments, the system 10 may use the time required for the tracer to reach the heart after administration, the spread of the injection as it moves through the lungs, the transit time of the heart, time and distribution of recirculation, uptake and metabolization rates in various tissues, rates of removal from the blood stream, absorption and elimination of the tracer in tissues and organs such as the liver and kidney to determine PK/PD parameters used in analyzing the images acquired during the procedure. In particular embodiments, the system 10 may relate various times involved in the procedure in setting parameters such as injection flow rates to optimize data collection and analysis. The times may include, for example, transit time and bolus broadening from injection site to central circulation, transit time through the lungs, and recirculation and distribution times. FIGS. 7a through 7e illustrates this phenomena. FIGS. 7a and 7b represent Hounsfield units measurements in the pulmonary artery and aorta respectively for a number of patients who received a 20 ml injection of contrast at 3 ml/S with a 20 ml saline flush at 3 ml/S. The patient to patient variation is evident. FIGS. 7c, 7d, and 7e represent aortic enhancements under the same conditions, illustrating the difference that the saline flush makes in helping to drive the drug, contrast, or tracer 141 to the central circulation.

In some embodiments, important times including, for instance, diffusion rates into and out of blood cells, diffusion rate into and out of extravascular or extracellular space, and diffusion rate into and out of cells, may also be utilized in setting parameters for the procedure. In other embodiments, coordination times including, for example, physiological events, imaging acquisition, first pass flow of the drug, and PK/PD phenomena times of interest can be utilized by the system to optimize parameters associated with the procedure.

For example, if the injection produces a very short or tight bolus the concentration of the tracer in the heart can become very high, and the input function at specific voxels may differ significantly from each other over time and differ from what can be measured in the larger blood vessels or the heart. As a result, imagers such as PET scanners cannot respond linearly to the tracer. Currently, imagers must approximate a linear response to provide accurate input functions over time; however, accurately estimating an image derived input function from a tight bolus can be difficult because frame rate of the scanner, activity of the tracer, and the noise associated with radioactive decay. Additionally, analysis of images acquired after bolus injection of tracer often treats data that is an integral of all the counts collected over the scan period as the intensity of the radiation source at a point in time, often the midpoint of the scan. With rapidly changing concentrations, the concentration measured can be significantly different than the instantaneous concentration, more when rising or less when falling. Thus, when trying to fit the data curve, treating the data as being an instantaneous point on the curve rather than as the integral of the curve over time can lead to significant errors. Thus, in some embodiments, it is preferable to operate in the time integral mode. In other embodiments it is preferable to operate in the list mode so that time partitioning can be determined after data acquisition.

Therefore, in certain embodiments, the tracer may be injected over a period of time. Without wishing to be bound by theory, steady improvement in PK/PD data derived from images acquired using the methods and systems described above may be achieved by injecting a tracer over a time period of about 30 seconds, about 60 seconds, about 120 seconds, about 240 seconds, about 360 seconds, and so on and any time period between these exemplary time periods. In other embodiments, a decaying exponential flow profile for the injection of tracer may be used. In still other embodiments, continuous infusion of the tracer may be used, and in some embodiments, continuous infusion may include a bolus injection at the beginning of the procedure. Without wishing to be bound by theory, a continuous infusion with bolus injection procedure may be beneficial where rapid metabolism of the tracer may occur to achieve and maintain the desired blood plasma level as is done in neurotransmitter studies.

In particular embodiments, a tracer may be delivered over a time that is longer than the average or mean circulation time of the tracer in the blood to provide a blood pool concentration that is relatively uniform. The whole blood concentration of the tracer can be measured in the heart or a large artery, and the whole blood concentration can be measured as the blood leaves the kidney, using a constant for the clearance rate of the kidney. In patients with healthy kidneys, the kidneys are an important excretory pathway for tracers such as FDG. For appropriate tracers, the concentration after the filtration by the kidneys therefore can be assumed to be low, approaching the concentration in the blood cells, which make up approximately 40% of the total blood volume as a check to or instead of using a population or standard calculation for determining plasma concentration from whole blood concentration. The plasma concentration can be determined based on the quantity, the central circulation whole blood concentration minus the post kidney venous whole blood concentration, that quantity divided by the extraction fraction of the kidney for that drug 141.

In some embodiments, the imaging system time scale may be used to determine an appropriate injection profile. In particular, systems such as CT and MR can acquire images in less than 1 second. However, PET images can be acquired with a high time resolution, but the images are noisy because the dose of radioactivity given determines the maximum average total count rate and short scans therefore include fewer decay events or counts. Thus, in some embodiments, the PET data may be acquired in "list mode" and archived in a table or list in memory by the system such that each event is time stamped. During subsequent analysis the data and events may be rebined or gathered into whatever time steps are optimum for the analysis. In such embodiments, injection of the tracer may be controlled and slowed as hand injections are often too fast in relation to this time scale.

In some embodiments, circulation and recirculation time of the patient may be used to determine an appropriate injection profile. Circulation and recirculation may affect the analysis in at least two ways. First, circulation time affects the ability of the control system 120 to use the central cardiac or arterial blood concentrations as the input function for other parts of the body because there is a time delay between the measurement of concentration in the central blood vessels and when that concentration reaches peripheral tissue. Second, recirculation time affects the buildup of the tracer in the blood.

Figure 2:
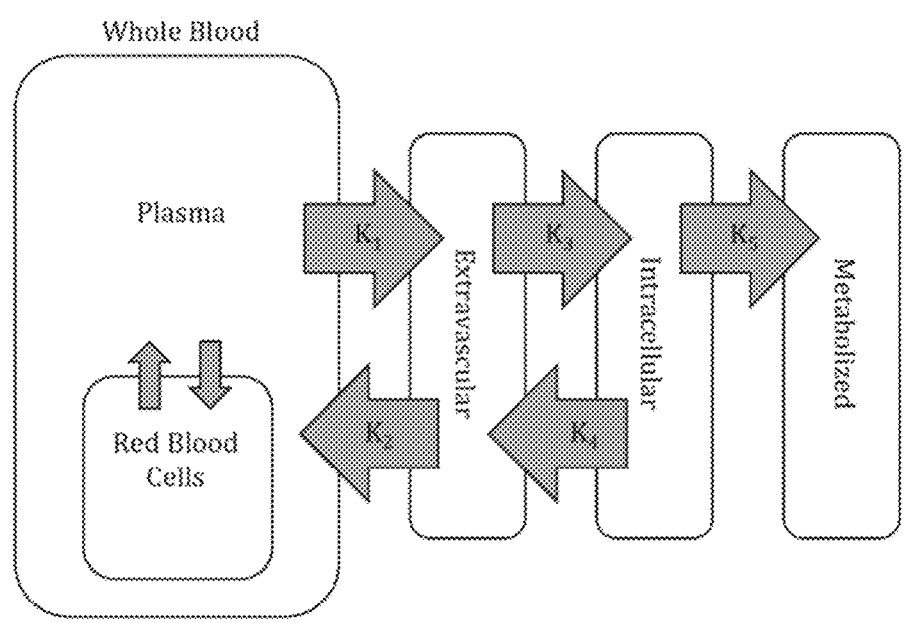
FIG. 2 is a flow chart representing the movement of a tracer from whole blood to a tissue and cells within the tissue.

In some embodiments, expected or estimated diffusion or transport coefficients of the tracer from the plasma into the target tissue ($K_1$), from the target tissue into the plasma ($K_2$), from the target tissue into a cell of the target tissue ($K_3$), and from a cell into the target tissue ($K_4$) (see FIG. 2) can be used to determine an appropriate injection profile. Generally, when $K_1$ or $K_3$ are slow or $K_2$ or $K_4$ are fast, a longer the scan may be required to acquire useable data. As such, a longer injection time may be used, and in certain embodiments, continuously varying or step function changes that are maintained for a sufficient time may be included.

In some embodiments, rate of removal of tracer from the blood pool may be used to determine an appropriate injection profile. Tracer can be removed from the blood pool through excretion by the kidneys or liver, dialysis, metabolism to byproducts, or uptake by tissue other than that of interest. For tracers that are removed from the blood pool quickly, longer injection profiles may be required to acquire useable data.

In particular embodiments, iterative reconstruction or other numerical techniques may be utilized by the controller system 120 during the analysis process and/or results from previous external modeling and analysis can be used to model or predictable adapt some or all of the total system including the tracer used, the imaging apparatus, and the data reconstruction/analysis process enabling optimum or sufficient injection to be delivered given known or estimated information about the patient and the other parts of the total system. In various embodiments, iterative reconstruction techniques during analysis can partially or fully include, compensate for, or overcome a number of non-idealities or non-linearities in the overall system. For example, PK/PD model limitations such as extraction fraction, receptor or transporter saturation, the concentration of tracer in the tissue over time, limited count statistics, and the like can be optimized using previous data so that image acquisition time with respect to count noise and time resolution can be resolved.

Example factors that can be included as inputs to procedure plan and/or analysis are the disease or condition for which patient is being studied, anticipated model or analysis to be used or parameters to be determined, patient factors, levels of blood sugar or other relevant molecules. Example study factors include the tracer being used and other drugs or stimuli. Example imager factors which may be considered include the sensitivity, resolution, collimator characteristics, scatter, positron travel, and the various factors considered in iterative reconstruction algorithms in the literature and practice, slice integration or times, bed position timing, reconstruction algorithm, motion compensation. Further example factors include reconstruction and model factors, input function determination (including blood binding), circulation delay to tissue from input function, blood volume fraction, and superposition of multiple tissue types in one voxel or volume of analysis.

In general, using a controlled injector to deliver one or more drugs as part of the protocol of the system 10 has numerous benefits. Injectors can do what may be difficult or impossible to do manually, such as inject at higher pressures, inject at higher flow rates, inject higher total volumes, inject higher viscosity materials (utilizing the high pressure capability), synchronize injection with other equipment, inject consistently over time, inject slowly & steadily (early liver metastases, gene therapy) inject very rapidly, and inject consistently where material properties vary over time and varying the injection under program control. An injector can overcome or maintain consistent performance in the face of variations in fluid path restrictions, viscosity, operator variations, patient variations, venous volume, topography, and flow rates, and central blood volume and cardiac output. Parameters which can be controlled include for example volume, flow rate, pressure, temperature, selection of fluid(s), concentration-simultaneous injection to maintain constant total flow, state of fluids (temperature, agitation, viscosity), time sequencing of any of above, pause, hold, and delay.

EXAMPLES

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples.

Example 1

Figure 3A:
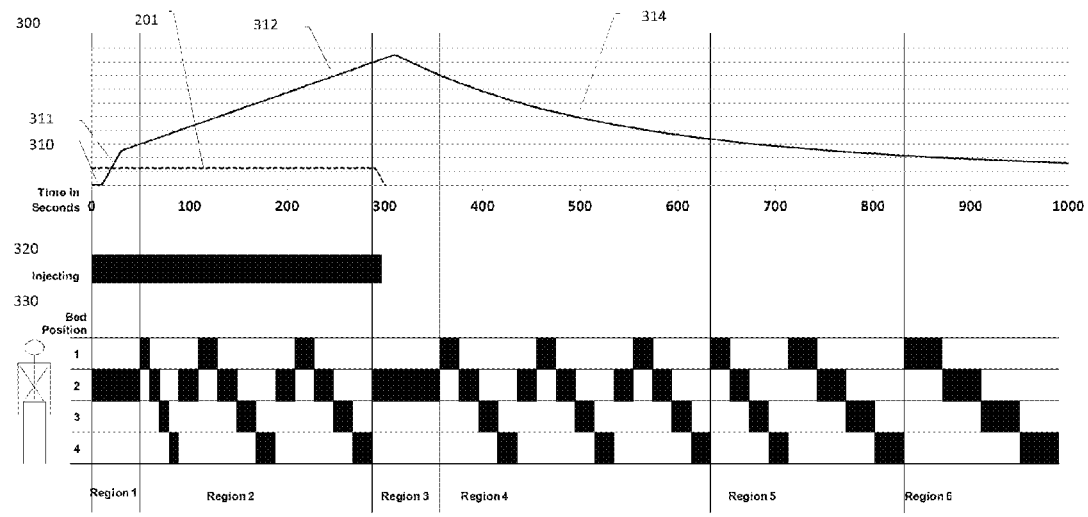
FIGS. 3a and 3b are a graphical representation of two exemplary methods of the invention.

FIG. 3a shows an exemplary protocol for system 10 of various embodiments. The graph 300 is a curve representing the drug concentration in the left ventricle or the ascending aorta over time. The horizontal axis provides time in seconds and vertical scale is in arbitrary units, which would depend upon the drug being given and the imaging modality being used, for example mCi/ml for nuclear medicine, Hounsfield units for CT, T1 or T2 for MR, amplitude for ultrasound, and so on. The dashed line 201 indicates the injection rate of the tracer. The bar 320 below the graph 300 indicates injection (black) versus no injection (white). Bed position during the scan 330 is provided below the injection graph. Because the scanner can cover only a finite volume of the body, the patient is generally scanned in overlapping steps or positions of the patient bed, thus the term "bed positions." Four bed positions are provided in FIG. 3. Bed position 1 covers the head and shoulders; bed position 2 covers the heart and torso; bed position 3 covers the lower torso and upper legs; and bed position 4 covers the remainder of the legs. If the scanner is not large enough to cover the whole body in 4 bed positions, the operator can choose to add additional bed positions and/or shorten the time at each bed position.

As illustrated in FIG. 3a, injection is constant over 300 seconds, or 5 minutes, shown on the bar graph 320. As shown on the line graph 300, for an injection that starts at time 0, there is a period of time 310 before any tracer is observed at the ascending aorta. The concentration of tracer n the plasma is 0. A rapid rise in tracer is then observed 311 as the bolus reaches the aorta and achieves full flow. A linear rise in tracer the concentration is observed 312 as the tracer builds up in the blood as it is recirculated. The tracer is expected to be moving out of the blood into various tissues and organs at this time, so the rise in concentration is not exactly linear. However, for the purposes of this example, it will be illustrated by a straight line. Finally, after the injection ceases, normal diffusion and elimination of the tracer from the blood is indicated by the decrease in plasma concentration 314. As discussed above, the concentration of tracer in the plasma is different than the concentration in whole blood because of uptake (or lack of uptake) by red blood cells. The control system can be configured to determine the plasma concentration by monitoring tracer concentration of blood leaving the kidney or by various other methods known to those skilled in the art.

The bed position 330 illustrated in FIG. 3*a*, is selected to provide a purposeful and non-uniform method to achieve accuracy of the determination of the input function and still enable enough points for a quantitative analysis to be done on a voxel basis. In Region 1, the scan is strictly over the left ventricle, the aorta, or another region chosen by the operator to provide the input function. This enables the imaging system 110 to assess the plasma concentration of the tracer during the scan.

Once the input function concentration level sets in the protocol, the protocol moves into Region 2. The patient support moves the patient to bed position 1 and a scan is taken of the head. Subsequently, the patient support is moved successively to bed positions 2, 3, and 4. Note that bed position 2 allows another assessment of the input function.

As the injection is ending, region 3 of the protocol begins, and the patient support returns to bed position 2 so that the input function region can be measured during the transition from climbing to decaying blood plasma levels. This example protocol involves monitoring the end of the rise and the beginning of the fall.

After a sufficient time, region 4 begins, in which all the bed positions are scanned. In the example protocol of FIG. 3*a*, three data scans are taken for each bed position and extra are taken of the bed position with the input function region. This example protocol indicates that the first 4 bed positions are scanned at half the rate of the subsequent ones. This can be adjusted based upon the expectations of the operator, the capabilities of the imaging system 110, or adaptively based upon the measurements or image reconstructions, most simply based upon a total count. In this case the earlier scans could be slower than the latter, which is opposite of what is illustrated in the example of FIG. 3*a*. As the level in the blood decrease and changes more slowly, there is no need for the extra measurements of the input function.

The protocol enters Region 5 where a series of scans from head to foot are taken. During region 5, the length of scan at each bed position can vary from the length of time from the time periods of region 4. For example, the time period for each bed position scan can be selected from a library or manually fixed by the operator. In other embodiments, the imager or analysis algorithm run by the control system can select the time period for each scan based on patient and imager information.

Region 6 represents a final longer scan time at each bed position. The concentration of tracer in the target tissue will change most slowly at this time, so longer scan times will provide lower noise measurement while not missing any significant dynamic information. This could be used to create an image that the operator or doctor would consider to be the normal static image used for visual diagnosis, such as looking for unknown or distant metastases.

During the imaging sequence the control system may simultaneously collect information from the one or more auxiliary sensors that can be used to condition the image data. For example, if the auxiliary sensor is collecting ECG data, it can be used to link data or images from the region of the heart to the heart cycle. If the left ventricle is being used for input function determination, only data collected during diastole can be used to minimize interference from the heart wall. If the auxiliary sensor is measuring respiration, it can be used in the analysis to select data during the end tidal phase, or to the extent possible to correct for patient motion. Where the imager is a PET/MR system, anatomical data from the MR image can be simultaneously collected with the PET data and used by the control system to compensate for motion, even including intestinal or other physiological motion that cannot be measured or sensed externally.

The analyzer uses the data from the imaging system 110 to first determine the input function and then to conduct the analysis determined by the operator. Among the more sophisticated analysis is a voxel by voxel, or at least a region of interest, multi-compartmental PK/PD analysis. Among the less sophisticated analysis would be a Patlak analysis. The least sophisticated would be a simple SUV corrected for residual blood concentration. The nuclear medicine literature contains many sophisticated and simple approaches. PMOD mentioned elsewhere is a commercially available package. The protocol of this example includes relatively complete or full information about the input, allowing the most sophisticated modeling or analyses to be performed.

Example 2

Figure 3B:
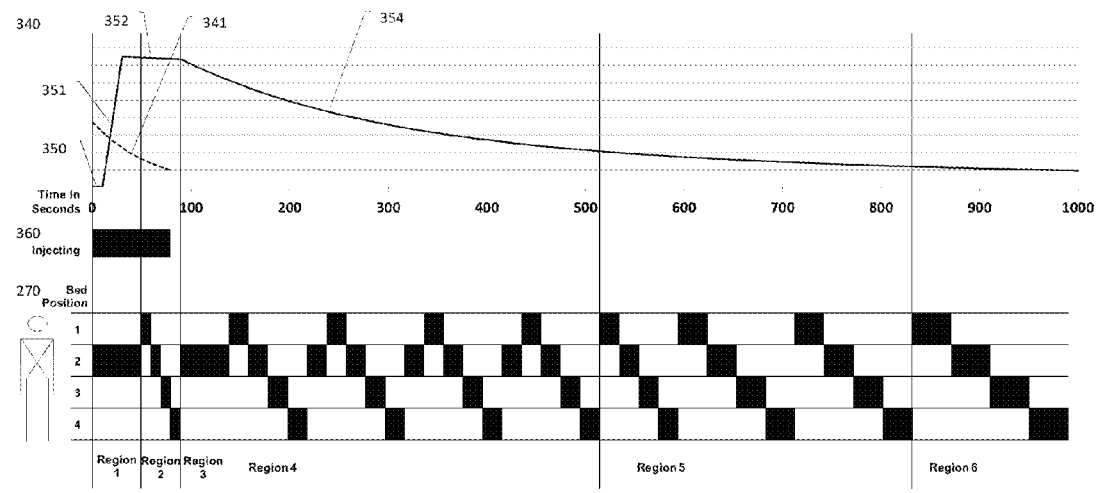

The protocol of FIG. 3*b* is used and the control system is employing a Patlak analysis to perform the quantitative analysis. This protocol uses a decaying exponential injection protocol selected to increase the blood concentration to a high level and hold it steady for approximately 90 seconds. Graph 340 represents this process, with dashed line 341 indicating the injection rate of the tracer. As above, injection of the tracer creates a blood concentration, which initially is 0, 350, until the tracer achieves an observable concentration at the site being measured for the input function. The tracer concentration then quickly rises 351 and holds steady 352 before decaying 354 after the injection 360 stops. In region 1, the input function volume is measured, as well as the other patient voxels in that bed position 270. Once the concentration reaches the plateau region and is not changing quickly, a scan through all the bed positions is carried out in region 2 to get an initial measurement for each voxel. In region 3, the input function is measured as the injection ends and the tracer concentration in the blood begins to fall. In region 4, the concentration in the blood is changing rapidly enough that it is worth oversampling the input function bed position. In region 5, the concentration is changing slowly enough that the extra sampling of the input function is not needed, and in region 6, a long scan of all the bed positions is carried out.

Once the scan is completed, the control system applies Patlak analysis to each voxel to measure the glucose metabolic rate of the tissue. This can be used in the diagnosis of disease or in the assessment of the disease's response to treatment. For the Patlak analysis, it is not necessary to measure the concentration in the tissue voxels from the beginning of the scan because the data that is of most importance is that measured once a general equilibrium has been reached between blood and tissue concentrations, at which time the irreversible metabolic process is the primary factor affecting the increase in the ration of tissue concentration to plasma concentration. Patlak analysis does, however, require an accurate measurement of the input function over the whole time. The decaying exponential bolus delivered over 90 seconds is selected as a compromise or happy medium between these two factors. The faster the drug is delivered, the sooner the stabilization process begins and the shorter the total scan time can be. However, it is necessary to accurately know the integral of the concentration curve, so starting with a rapid climb to too high a concentration can cause errors in input function estimation and integration. A very slow or long injection such as that of FIG. 3*a*, while easy to measure and integrate, means that the stabilization of the decay does not start happening until 5 minutes into the scan, which is a needless wait if the control system is only applying a Patlak analysis.

Example 3

A third example protocol for which the integrated system 10 can be use is shown in FIGS. 4a through 4c. This is a SPECT myocardial perfusion imaging (MPI) study. The imaging system 110 being used is one of the newer dedicated cardiac SPECT units with solid state CZT detectors. In this protocol, 3 different drugs or fluids are being injected, Lexiscan, which is a pharmaceutical stress agent, saline which is used to push fluids through tubing, and the thallium, which is a radiopharmaceutical used in MPI studies. FIG. 4a shows the general timeline of the procedure. Lexiscan is delivered slowly over 25 seconds. There is a 25 second delay during which saline is delivered to ensure all the Lexiscan is flushed from the tubing and to give it time to act on the heart, then thallium is delivered rapidly over 30 seconds and finally there is a saline flush at the same rate to ensure that all the thallium is delivered to the patient.

FIG. 4b shows the disposable fluid path that enables 3 fluids to be delivered with a pump with two syringes. The A syringe holds the radiopharmaceutical diluted to 30 ml. The B syringe is filled with saline. The 5 ml of Lexiscan is staged by placing it in the tubing. The table in FIG. 4c illustrates in detail how the injector could be programmed to accomplish this protocol. When the B syringe first dispenses saline at 0.2 ml/S, it is actually delivering the Lexiscan to the patient. In the next phase, syringe B is delivering saline to the patient at the same flow rate. Then syringe A with the thallium delivers the thallium to the patient at 1 ml/S. This is followed by syringe B delivering saline at 1 ml/S to completely flush the tubing set.

Example 4

Figure 5A:
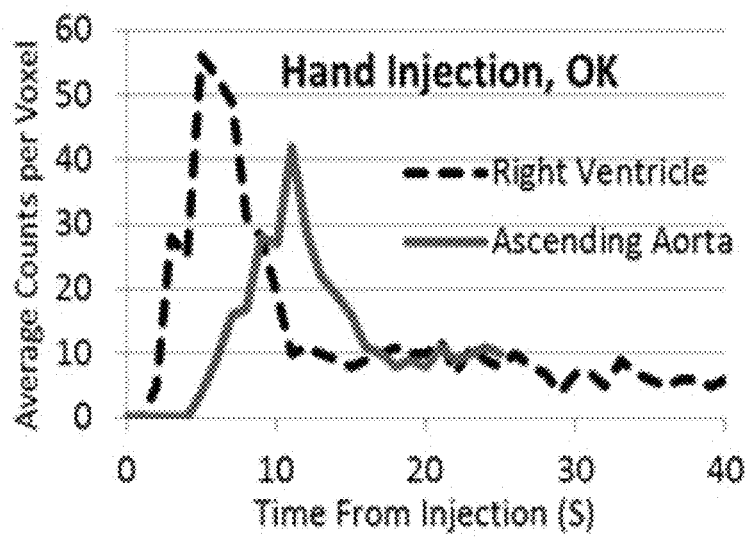
FIG. 5a shows good results.
Figure 5B:
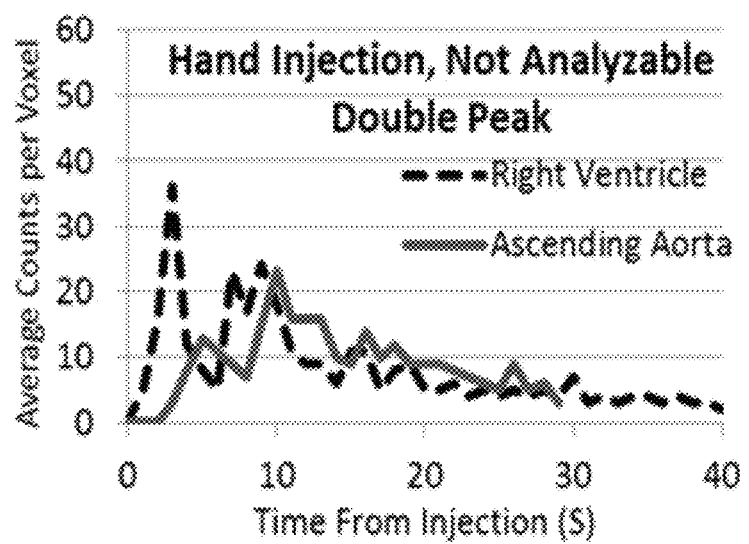
FIG. 5b shows poor results.
Figure 5C:
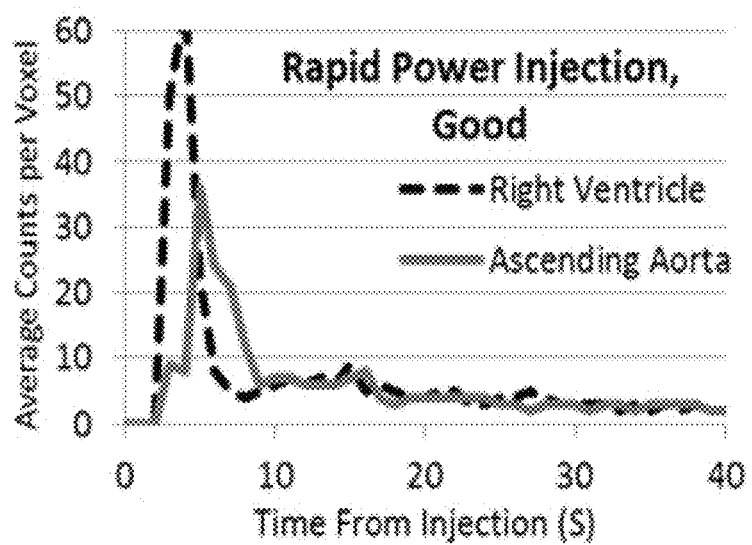
FIG. 5c shows good results.

In other study, for example a first pass cardiac imaging procedure, it is desirable to have a very sharp, tight bolus of the MPI imaging drug and observe it move through the heart. This facilitates the separation of the left ventricle blood pool from blood in the muscle tissue when doing simple analysis and quantification of myocardial perfusion reserve. FIGS. 5a and 5b show measurements of two-hand injection. The common method for delivering a hand bolus of tracer for MPI is to connect two syringes to a stopcock with the output of the stopcock connected directly to an IV line or a tube going to the IV. The stress agent is injected, and the stopcock is quickly changed to allow saline to be pulled into the drug syringe. The stopcock is moved again, and the saline from the drug syringe is injected into the patient to flush the line and the patient's veins. If it is essential to achieve a tight bolus, the saline is delivered directly to the patient rather than being used to rinse out the drug syringe. The injection illustrated in FIG. 5a is a sufficiently sharp bolus to accurately compute myocardial flow reserve while the injection shown in FIG. 5b has a double hump or peak, which prevents the quantification of myocardial flow reserve. The injection of FIG. 5c was delivered with a small volume of drug, less than 1 ml, staged into tubing and pushed at a high flow rate so that a consistent narrow bolus was achieved. This enables every study to be diagnostic, to lead to a useful assessment of myocardial flow reserve.

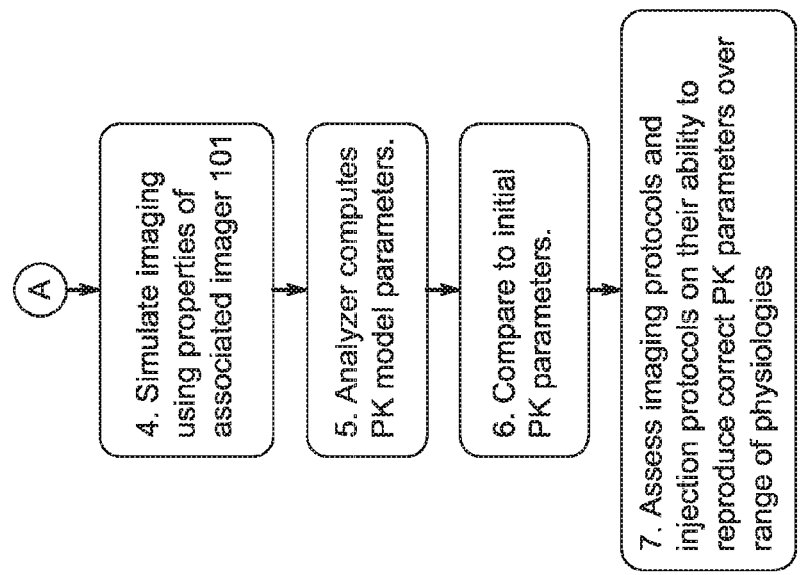

The invention claimed is:

1. A method for imaging tissue, the method comprising:
administering a tracer;
imaging at least two regions of a body, wherein the at least two regions of the body cannot be imaged simultaneously;
determining an input function for the tracer by imaging a first region of the body during selected times;
using an injector to administer the tracer in a manner that accurately estimates the input function when said first region is not being imaged;
imaging one or more additional regions of the body to create imaging data;
estimating the input function from all information gathered; and
estimating one or more parameters from each additional region of the body based on the input function and the imaging data gathered from each region.

2. The method of claim 1, wherein administering the tracer comprises bolus injection of the tracer.

3. The method of claim 1, wherein administering the tracer comprises slow injection of the tracer over a period of time.

4. The method of claim 3, wherein the period of time comprises a time period selected from the group consisting of about 30 seconds, about 60 seconds, about 120 seconds, about 240 seconds, and about 360 seconds.

5. The method of claim 1, wherein administering the tracer comprises delivering the tracer over a time that is longer than an average circulation time of the tracer in a patient's blood stream.

6. The method of claim 1, wherein administering the tracer comprises a bolus injection of a first amount of the tracer followed by an infusion of a second amount of the tracer.

7. The method of claim 1, wherein determining the input function comprises determining a plasma concentration of the tracer in the first region of the body during the selected times.

8. The method of claim 7, wherein determining the plasma concentration of the tracer in the first region of the body during the selected times comprises determining a concentration of tracer for whole blood, determining a concentration of tracer for red blood cells, and subtracting the concentration of tracer for red blood cells from the concentration of tracer from whole blood.

9. The method of claim 1, further comprising identifying a maximum blood value after administering the tracer and before determining the input function.

10. The method of claim 1, wherein determining the input function is carried out using only image data.

11. The method of claim 1, further comprising administering a second dose of the tracer.

12. The method of claim 1, wherein the input function is estimated by a process selected from the group consisting of determining a plasma concentration of the tracer, determining a time required for the tracer to reach a patient's heart after administration, determining a time required for spread of the tracer through a patient's lungs, determining a transit time of the patient's heart, determining a time and distribution of circulation or recirculation, determining uptake and metabolization rates of the tracer in various tissues, determining rates of removal of the tracer from a patient's blood stream, determining absorption and elimination of the tracer in tissues and organs, determining diffusion rates into and out of blood cells, determining diffusion rates into and out of extravascular and extracellular spaces, determining diffusion rates into and out of cells, determining a time scale of an imaging system, and combinations of any thereof.

13. The method of claim 1, further comprising determining coordination times to optimize at least one PK/PD parameter associated with the imaging.

14. The method of claim 13, wherein the coordination times are physiological event times, imaging acquisition times, first pass flow times of a drug, PK/PD phenomena times or combinations of any thereof.

15. The method of claim 1, further comprising utilizing iterative reconstruction techniques during analysis to at least partially compensate for one or more non-idealities or non-linearities in an imaging system.

16. The method of claim 1, further comprising normalizing imaging data based on multiple input functions determined throughout a procedure.

* * * * *

UNITED STATES PATENT AND TRADEMARK OFFICE
CERTIFICATE OF CORRECTION

| | |
|---|---|
| PATENT NO. | : 9,436,989 B2 |
| APPLICATION NO. | : 14/123390 |
| DATED | : September 6, 2016 |
| INVENTOR(S) | : Uber et al. |

It is certified that error appears in the above-identified patent and that said Letters Patent is hereby corrected as shown below:

On the Title Page

Delete the title page and substitute therefor with the attached title page consisting of the corrected illustrative figure(s).

In the Drawings

Please replace FIGS. 1-7E with FIGS. 1-7E as shown on the attached pages.

In the Specification

In Column 6, Line 61, delete "imaging (MR)" and insert -- (MR) --, therefor.
In Column 9, Line 24, delete "an user" and insert -- a user --, therefor.
In Column 11, Line 12, delete "131I-iodide, 131I-iodide," and insert -- 131I iodide," --, therefor.
In Column 13, Line 26, delete "units" and insert -- unit --, therefor.

Signed and Sealed this
Tenth Day of January, 2017

Michelle K. Lee
*Director of the United States Patent and Trademark Office*

(12) United States Patent
Uber, III

(10) Patent No.: US 9,436,989 B2
(45) Date of Patent: Sep. 6, 2016

(54) SYSTEM AND METHOD FOR RAPID QUANTITATIVE DYNAMIC MOLECULAR IMAGING SCANS

(75) Inventor: Arthur E. Uber, III, Pittsburgh, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 230 days.

(21) Appl. No.: 14/123,390

(22) PCT Filed: Jun. 4, 2012

(86) PCT No.: PCT/US2012/040755
§ 371 (c)(1),
(2), (4) Date: Dec. 12, 2013

(87) PCT Pub. No.: WO2012/167257
PCT Pub. Date: Dec. 6, 2012

(65) Prior Publication Data
US 2014/0119621 A1    May 1, 2014

Related U.S. Application Data

(60) Provisional application No. 61/493,142, filed on Jun. 3, 2011, provisional application No. 61/629,414, filed on Nov. 18, 2011.

(51) Int. Cl.
*G06K 9/00* (2006.01)
*G06T 7/00* (2006.01)
(Continued)

(52) U.S. Cl.
CPC ............ *G06T 7/0012* (2013.01); *A61B 6/032* (2013.01); *A61B 6/037* (2013.01); *A61B 6/481* (2013.01);
(Continued)

(58) Field of Classification Search
USPC .................................... 382/128–134
See application file for complete search history.

(56) References Cited

U.S. PATENT DOCUMENTS

| 3,191,789 A | 6/1965 | Davidson |
| 4,092,546 A | 5/1978 | Larrabee |

(Continued)

FOREIGN PATENT DOCUMENTS

| FR | 2867084 A1 | 9/2005 |
| WO | 2006129301 A2 | 12/2006 |
| WO | 2009042577 A2 | 4/2009 |

OTHER PUBLICATIONS

International Search Report with Written Opinion for International Application No. PCT/US2012/040755 mailed on Aug. 10, 2012.
(Continued)

*Primary Examiner* — Alex Liew
(74) *Attorney, Agent, or Firm* — Joseph L. Kent; David Schramm; James R. Stevenson

(57) ABSTRACT

Methods and systems for controlled administration of a tracer and quantification of uptake of the tracer by a target organ are described. The method includes administering a tracer to a patient and imaging at least two regions of the patient's body that cannot be imaged simultaneously. An input function for the tracer can be determined by imaging a first region of the patient's body during selected times, and using an injector to administer the tracer in a manner that accurately estimates the input function when this first region is not being imaged. One or more additional regions of the body may then be imaged to create data that may be used to estimate the input function. One or more parameters may then be estimated from each additional region of the body based on the input function and the imaging data gathered from each region.

16 Claims, 12 Drawing Sheets

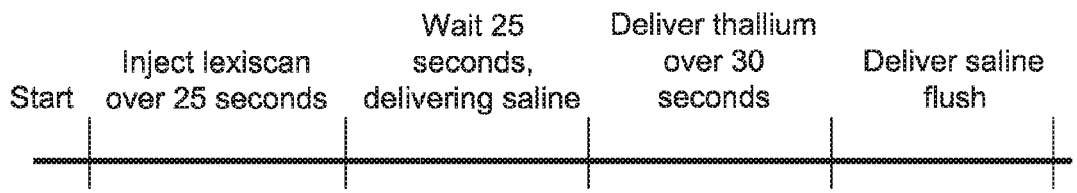
FIG. 4a
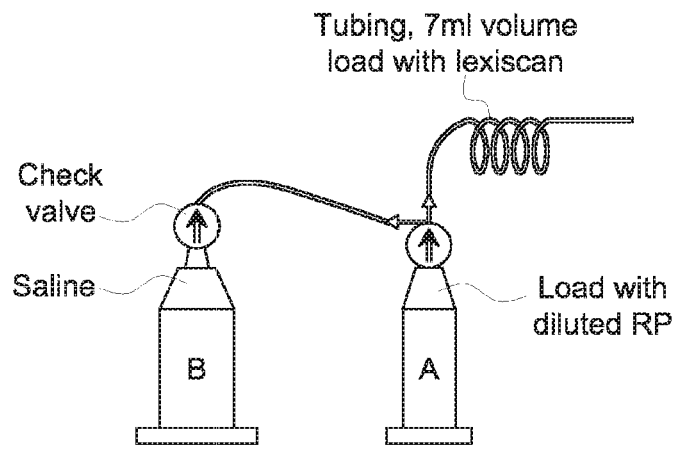
FIG. 4b
| Purpose | Phase | Volume | Flow rate | Duration |
|---|---|---|---|---|
| Deliver lexiscan | B | 5 ml | 0.2 ml/S | 25 S |
| Delay - push residuals from vein & tubing. | B | 5 ml | 0.2 ml/S | 25 S |
| Delay - There will be about a 7 second delay before the thallium reaches the distal connector. Note: There should inherently be a small bubble at the start of the thallium. | | | | 7 S |
| Deliver thallium | A | 30 ml | 1 ml/S | 30 S |
| Push residuals from vein & tubing. | B | 30 ml | 1 ml/S | 30 S |
FIG. 4c